(12) United States Patent
Eyal et al.

(10) Patent No.: US 7,678,547 B2
(45) Date of Patent: Mar. 16, 2010

(54) VELOCITY INDEPENDENT ANALYTE CHARACTERIZATION

(75) Inventors: Shulamit Eyal, Givat-Shmuel (IL); Stephen Quake, Stanford, CA (US)

(73) Assignee: California Institute of Technology, Pasadena, CA (US)

(*) Notice: Subject to any disclaimer, the term of this patent is extended or adjusted under 35 U.S.C. 154(b) by 126 days.

(21) Appl. No.: 09/970,453

(22) Filed: Oct. 2, 2001

(65) Prior Publication Data
US 2002/0123033 A1 Sep. 5, 2002

Related U.S. Application Data

(60) Provisional application No. 60/237,937, filed on Oct. 3, 2000.

(51) Int. Cl.
*G01N 33/53* (2006.01)
(52) U.S. Cl. ............... 435/7.21; 435/7.1; 435/7.92; 436/500; 436/518
(58) Field of Classification Search ............... 435/7.1, 435/7.21, 7.92; 436/500, 518
See application file for complete search history.

(56) References Cited

U.S. PATENT DOCUMENTS

| 3,570,515 | A | 3/1971 | Kinner |
| 3,747,628 | A | 7/1973 | Holster et al. |
| 4,046,159 | A | 9/1977 | Pegourie |
| 4,119,368 | A | 10/1978 | Yamazaki |
| 4,153,855 | A | 5/1979 | Feingold |
| 4,245,673 | A | 1/1981 | Bouteille et al. |
| 4,434,704 | A | 3/1984 | Surjaatmadja |
| 4,898,582 | A | 2/1990 | Faste |
| 4,992,312 | A | 2/1991 | Frisch |
| 5,085,562 | A | 2/1992 | Van Lintel |
| 5,088,515 | A | 2/1992 | Kamen |
| 5,096,388 | A | 3/1992 | Weinberg |
| 5,126,115 | A | 6/1992 | Fujita et al. |
| 5,164,558 | A | 11/1992 | Huff et al. |
| 5,171,132 | A | 12/1992 | Miyazaki |
| 5,224,843 | A | 7/1993 | Van Lintel |
| 5,259,737 | A | 11/1993 | Kamisuki et al. |
| 5,265,327 | A | 11/1993 | Faris et al. |
| 5,290,240 | A | 3/1994 | Horres, Jr. |
| 5,336,062 | A | 8/1994 | Richter |
| 5,346,372 | A | 9/1994 | Naruse et al. |
| 5,375,979 | A | 12/1994 | Trah |
| 5,376,252 | A | 12/1994 | Ekstrom |
| 5,400,741 | A | 3/1995 | DeTitta et al. |
| 5,423,287 | A | 6/1995 | Usami et al. |
| 5,529,465 | A | 6/1996 | Zengerle et al. |
| 5,593,130 | A | 1/1997 | Hansson et al. |
| 5,642,015 | A | 6/1997 | Whitehead et al. |
| 5,659,171 | A | 8/1997 | Young et al. |
| 5,660,370 | A | 8/1997 | Webster |
| 5,681,024 | A | 10/1997 | Lisec et al. |
| 5,705,018 | A | 1/1998 | Hartley |
| 5,759,014 | A | 6/1998 | Van Lintel |
| 5,775,371 | A | 7/1998 | Pan et al. |
| 5,788,468 | A | 8/1998 | Dewa et al. |
| 5,836,750 | A | 11/1998 | Cabuz |
| 5,842,787 | A | 12/1998 | Kopf-Sill et al. |
| 5,875,817 | A | 3/1999 | Carter |
| 5,876,187 | A | 3/1999 | Afromowitz |
| 5,932,799 | A | 8/1999 | Moles |
| 5,942,443 | A | 8/1999 | Parce et al. |
| 6,007,309 | A | 12/1999 | Hartley |
| 6,043,080 | A | 3/2000 | Lipshutz et al. |
| 6,123,769 | A | 9/2000 | Sanjoh |
| 6,155,282 | A | 12/2000 | Zachary et al. |
| 6,174,365 | B1 | 1/2001 | Sanjoh |
| 6,296,673 | B1 | 10/2001 | Santarsiero et al. |
| 6,345,502 | B1 | 2/2002 | Tai et al. |
| 6,409,832 | B2 | 6/2002 | Weigl et al. |
| 6,524,790 | B1 * | 2/2003 | Kopf-Sill et al. ............ 435/6 |
| 6,613,512 | B1 * | 9/2003 | Kopf-Sill et al. ............ 435/6 |
| 6,767,706 | B2 | 7/2004 | Quake et al. |

FOREIGN PATENT DOCUMENTS

| EP | 0 592 094 A2 | 4/1994 |
| EP | 0 706 004 A2 | 4/1996 |
| EP | 0 779 436 A2 | 6/1997 |
| EP | 0 829 360 A2 | 3/1998 |
| EP | 0 845 603 A1 | 6/1998 |
| EP | 0 999 055 A2 | 5/2000 |
| GB | 2 155 152 A | 9/1985 |
| GB | 2 308 460 A | 6/1997 |
| JP | 07049301 A * | 2/1995 |

(Continued)

OTHER PUBLICATIONS

Armstrong et al. "Suspension Arrays for High Throughput, Multiplexed Single Nucleotide Polymorphism Genotyping." Cytometry, 2002, 40, 102-108.*

(Continued)

*Primary Examiner*—Lisa V Cook
(74) *Attorney, Agent, or Firm*—Townsend and Townsend and Crew LLP

(57) ABSTRACT

The present invention provides apparatuses for determining velocity independent analyte characteristic parameters and methods for using the same. In one particular aspect, the present invention provides a velocity independent flow cytometry.

8 Claims, 8 Drawing Sheets

FOREIGN PATENT DOCUMENTS

| | | |
|---|---|---|
| WO | WO 98/07069 A1 | 2/1998 |
| WO | WO 99/00655 A2 | 1/1999 |
| WO | WO 99/04361 A1 | 1/1999 |
| WO | WO 99/17093 A1 | 4/1999 |
| WO | WO 99/52633 A1 | 10/1999 |
| WO | 99/61888 A2 | 12/1999 |
| WO | WO 00/00678 A1 | 1/2000 |
| WO | WO 00/43748 A1 | 7/2000 |
| WO | WO 00/60345 A1 | 10/2000 |
| WO | WO 01/09595 A2 | 2/2001 |
| WO | WO 01/09595 A3 | 2/2001 |

OTHER PUBLICATIONS

Squire et al. "Multiple frequency fluorescence lifetime imaging microscopy." Journal of Microscopy, vol. 192, Pt.2, Feb. 2000, 136-149.*

Crabtree et al. (Analytical Chemistry, 1999, 71, 2130-2138).* van der Moolen et al. (Journal of Chromatography A, vol. 744, 1996, pp. 103-113).*

Sandia National Laboratories, MEM bibliography, BIOMEMS/mFluidics, pp. 1-2, Oct. 1998.*

SAND 2001-3412P.*

Khoo and Liu., 22$^{nd}$ Annual EMBS, Jul. 23-28, 2000. Chicago, IL, pp. 2394-2397.*

Lessard et al., CAT.INIST., A scanning apertureless fluoroescence microscope, 1999.*

Maluf, N., XP-0021517476, 2000, p. 42, An Introduction to Microelectromechanical Systems Engineering, Artech House Publishers, Boston, London.*

Marc A. Unger et al., Science, 2000, 288, 113-116.

Anne Y. Fu et al., Nature Biotechnology, 1999, 17, 1109-1111.

Stephen R. Quake et al., Science, 2000, 290, 1536-1540.

Hou-Pu Chou et al., Proc. Natl. Acad. Sci. USA, 1999, 96, 11-13.

David P. Schrum et al., Anal. Chem., 1999, 71, 4173-4177.

James B. Knight et al., Am. Physical Soc., 1998, 80, 3863-3866.

Chia-Fu Chou et al., Electrophoresis, 2000, 21, 81-90.

Jun Kameoka et al., Sensors and Actuators B, 2001, 77, 632-637.

Paul C.H. Li et al., Anal. Chem., 1997 69, 1584-1568.

J.G. Santiago et al., Expirments in Fluids, 1998, 25, 316-319.

Susan L. R. Barker et al., Anal. Chem., 2000, 72, 5925-5929.

Anup K. Singh et al., Anal. Chem., 2001, 73, 1057-1061.

Yien C. Kwok et al., Anal. Chem., 2001, 73, 1748-1753.

H. John Crabtree et al., Anal. Chem. 1999, 71, 2130-2138.

Dryden et al., Hydrodynamics, Dover Publications, New York 1956, pp. 177-202.

Juleon M. Schins et al., Cytometry, 1999, 37, 230-237.

"Acousto-Optic Modulators," available at www.brimrose.com/acousto_modulators.html, Sep. 27, 2000.

"Acuosto-Optic Modulators" available at www.brimrose.com/acousto_modulators.html, Sep. 27, 2000.

Ahn et al., "Fluid Micropumps Based on Rotary Magnetic Actuators," Proceedings of 1995 IEEE Micro Electro Mechanical Systems Workshop (MEMS '95), held in Amsterdam, Netherlands on Jan. 29-Feb. 2, 1995, pp. 408-412.

Benard et al., "A Titanium-Nickel Shape-Memory Alloy Actuated Micropump," Proceedings of Transducers '97, 1997 International Conference on Solid-State Sensors and Actuators, held in Chicago, IL, Jun. 16-19, 1997, 1:361-364 (1997).

Brechtel et al.; "Control of the electroosmotic flow by metal-salt-containing buffers", J Chromatography A, 1995, pp. 97-105, vol. 716.

Bryzek et al.; "Micromachines on the March", IEEE Spectrum, 1994, pp. 20-31, vol. 31, No. 5.

Buchaillot et al.; "Silicon nitride thin films Young's modulus determination by an optical non-destructive method", Jpn. J Appl Phys, 1995, pp. L794-L797, vol. 36, No. 2:6B.

Chiu et al.; "Patterned Deposition of Cells and Proteins onto Surfaces by Using Three-Dimensional Microfluidic Systems", Proc. Natl. Acad. Sci., 2000, pp. 2408-2413, vol. 97, No. 6.

Delamarche et al.; "Patterned delivery of immunoglobulins to surfaces using microfluidic networks", Science, 1997, pp. 779-781, vol. 276.

Duffy et al. "Patterning Electroluminescence Materials with Feature Sizes as Small as 5 µm Using Elastomeric Membranes as Masks for Dry Lift-Off", Advanced Materials, 1999, pp. 546-552, vol. 11, No. 7.

Duffy et al. "Rapid Prototyping of Microfluidic Switches in Poly(dimethylsiloxane) and Their Actuation by Electro-Osmotic Flow" Journal of Microeng, 1999, pp. 211-217, vol. 9.

Duffy et al. "Rapid PrototypIng of Microfluidic Systems in Poly(dmethylsiloxane)", Analytical Chemistry, 1998, pp. 4974-4984, vol. 70, No. 23.

Effenhauser et al.; "Integrated capillary electrophoresis on flexible silicone microdevices: Analysis of DNA restriction fragments and detection of single DNA molecules on microchips", Anal. Chem, 1997, pp. 3451-3457, vol. 69.

Effenhauser et al.; "Integrated chip-based capillary electrophoresis", Electrophoresis, 1997, pp. 2203-2213, vol. 18.

Fahrenberg et al. "A microvalve system fabricated by thermoplastic molding", J Micromech Microeng, 1995, pp. 169-171, vol. 5.

Gass et al. "Integrated flow-regulated silicon micropump," Sensors and Actuators A Physical, 1994, p. 335-338, vol. 43.

Gerlach, T., "Pumping Gases by a Silicon Micro Pump with Dynamic Passive Valves," Proceedings of Transducers '97, 1997 International Conference on Solid-State Sensors and Actuators, held in Chicago, Il., Jun. 16-19, 1997, pp. 357-360, vol. 1.

Goll et al., "Microvalves with bistable buckled polymer diaphragms," J. Micromech. Microeng., 1996, pp. 77-79, vol. 6.

Gravesen et al.; "Microfluids—A Review", Journal Micromech Microeng, 1993, pp. 168-192, vol. 3.

Harrison et al., "Micromachining a Miniaturized Capillary Electrophoresis-Based Chemical Analysis System on a Chip," Science, 1993, pp. 895-897, vol. 261.

Hornbeck et al., "Bistable Deformable Mirror Device," Spatial Light Modulators and Applications 1988 Technical Digest Series, vol. 8, Postconference Edition, Summaries of papers presented at the Spatial Light Modulators and Applications Topical Meeting, Jun. 15-17, 1988, Optical Society of America, pp. 107-110.

Hosokawa et al., "Handling of Picoliter Liquid Samples in a Poly(dimethylsiloxane)-Based Microfluidic Device," Anal. Chem., 1999, 71(20):4781-4785.

Ikuta et al., "Three dimensional micro integrated fluid systems (MIFS) fabricated by stereo lithography," IEEE Kyushu Institute of Technology, 1994, pp. 1-6.

Jacobson et al., "High-speed separations on a microchip," Anal. Chem., 1994, 66(7):1114-1118.

Jacobson et al., "Microfluidic Devices for Electrokinetically Driven Parallel and Serial Mixing," Anal. Chem., 1999, 71(20):4455-4459.

Jerman, H., "Electrically-Activated, Normally-Closed Diaphragm Valves," Proceedings of Transducers '91, 1991 International Conference on Solid-State Sensors and Actuators, pp. 1045-1048 (1991).

Jung et al., "Chemical and Physical Interactions at Metal/Self-Assembled Organic Monolayer Interfaces," Critical Reviews in Solid State and Material Sciences, 1994, pp. 1-54, vol. 19, No. 1.

Kenis et al. "Microfabrication Inside Capillaries Using Multiphase Laminar Flow Patterning," Science, 1999, 285:83-85.

Kim, Enoch et al., "Micromolding in Capillaries: Applications in Material Science," J. American Chemical Society, 118:5722-5731 (1996).

Kopp et al. "Chemical Amplification: Continuous-Flow PCR on a Chip", Science, 1998, 280:1046-1048.

Kuhn et al. "Silicon Charge Electrode Array for Ink Jet Printing", IEEE Transactions on Electron Devices, 1978, pp. 1257-1260, vol. ED-25, No. 10.

Lin et al. "Free-Space Micromachined Optical Switches for Optical Networking," IEEE J. Selected Topics in Quantum Electronics, 1999, pp. 4-9, vol. 5, No. 1.

Lötters et al. "The mechanical properties of the rubber elastic polymer polydimethylsiloxane for sensor applications," J. Micromech. Microeng., 1997, 7:145-147.

Lucy et al., "Characterization of the Cationic Surfactant Induced Reversal of Electroosmotic Flow in Capillary Electrophoresis," Anal. Chem., 1998, pp. 300-305, vol. 68.

Maluf, N., An Introduction to Microelectromechanical Systems Engineering, Artech House Publishers, Boston London pp. 42-45, 2000.

Muller et al., "Surface-Micromachined Microoptical Elements and Systems," Proceedings of IEEE, 1998, 86(8):1705-1720.

Olsson et al., "Simulation Studies of Diffuser and Nozzle Elements for Valve-less Micropumps," Proceedings of Transducers '97, 1997 International Conference on Solid-State Sensors and Actuators, held in Chicago, Il., Jun. 16-19, 1997, 2:1039-1042 (1997).

Pethig & Markx "Applications of dielectrophoresis in biotechnology," Tibtech, 15:426-432 (1997).

Qin et al., "Photolithography with transparent reflective photomasks," J. Vac.Sci. Technology, 16(1):98-103 (1998).

Qin et al., "Elastomeric Light Valves**", Adv. Mater., 1997, pp. 407-410, vol. 9, No. 5.

Rapp. R., "LIGA micropump for gases and liquids," Sensors and Actuators A, 1994, pp. 57-61, vol. 40.

Roylance et al., "A Batch-Fabricated Silicon Accelerometer", IEEE Transactions on Electron Devices, Dec. 1979, pp. 1911-1917, vol. ED-26, No. 12.

Schasfoort et al., "Field-Effect Flow Control for Microfabricated Fluidic Networks," Science, 1999, 286:942-945.

Schueller et al., "Fabrication of glassy carbon microstructures by soft lithography," Sensors and Actuators, 72(2):125-139 (1999).

Shoji et al.; "Smallest Dead Volume Microvalves for Integrated Chemical Analyzing Systems", Proceedings of Transducers '91, 1991, pp. 1052-1055, San Francisco.

Shoji, S., "Fluids for Sensor Systems", Topics in Current Chemistry, 1998, pp. 162-188, vol. 194, Springer Verlag Berlin Heidelberg.

Smits, J.G., "Piezoelectric Micropump with Three Valves Working Peristaltically", Sensors and Actuators, 1990, pp. 203-206, vol. A21-A23.

Sohn et al., "Capacitance cytometry: Measuring biological cells one by one," PNAS, 97(20):10687-10690 (2000).

Tufte et al., "Silicon Diffused-Element Plezoresistive Diaphragms," J. Appl. Phys., Nov. 1962, 3322-3327, vol. 33, No. 11.

Ullmann's Encyclopedia of Industrial Chemistry, Sections 6 to 6.3, Topic: Carbon Black, Sixth Edition, 1999.

Van De Pol et al., "Micro Liquid Handling Devices—A Review", Micro Systems Technologies, 1990, pp. 799-805, vol. 90.

Van De Pol, F.C.M. et al. "A Thermo-Pneumatic Actuation Principle for a Microminiature Pump and Other Micromechanical Devices" Sensors and Actuators, May 3, 1989, pp. 139-143, vol. 17, Nos. 1-2.

Vieider et al.; "A Pneumatically Actuated Micro Valve with a Silicon Rubber Membrane for Integration with Fluid Handling Systems", Proceedings of Transducers '95, the 8th International Conference on Solid-State Sensors and Actuators and Eurosensors IX, held in Stockholm, Sweden on Jun. 25-29, 1995, 1995, pp. 284-286, Stockholm, Sweden.

Washizu et al., "Molecular Dielectrophoresis of Biopolymers," IEEE Transactions on Industry Applications, 1994, 30(4):835-843.

Xia et al., "Complex Optical Surfaces Formed by Replica Molding Against Elastomeric Masters," Science, 1996, 273:347-349.

Xia et al., "Soft Lithography," Angew. Chem. Int. Ed., 1998, 37:551-575.

Xia, Y. et al., "Micromolding of Polymers in Capillaries: Applications in Microfabrication," Chemistry of Materials, 8(7)1558-1567 (1996).

Yang et al. "A Mems Thermopneumatic Silicone Membrane Valve", Proceedings of IEEE 10th Annual International Workshop on MicroElectro Mechanical Systems, Sensors and Actuators, 1998, A64(1):101-108.

Yang et al., "A MEMS Thermopneumatic silicone Membrane Valve," Proceedings of the IEEE 10th Annual Workshop of Micro Electro Mechanical Systems Workshop (MEMS '97), held Jan. 26-30, 1997 in Nagoya, Japan, pp. 114-118 (1997).

Yazdi et al. "Micromachined Inertial Sensors," Proceedings of IEEE, 1998, 86(8)1640-1659.

Young et al. "Contoured elastic-membrane microvalves for microfluidic network integration," J. Biomechanical Engineering, 1999, 121:2-6.

Zengerle et al., "A Micro Membrane Pump with Electrostatic Actuation," 1992 IEEE Conf. on Micro Electro Mechanical Systems, held Feb. 4-7, 1992 in Travemunde Germany, pp. 19-24.

Zengerle et al., "Performance Simulation of Microminiaturized Membrane Pumps," from 7th International Conference on Solid-State Sensors and Actuators held Jun. 7-10, 1993 in Yokohama Japan, pp. 106-109.

"Chapter 9: Microfluidic Devices," Micromachined Transducers Sourcebook, pp. 779-882, 1998.

"Last Chance for Micromachines," The Economist Technology Quarterly, printed from website http://www.economist.com/science/displayStory.cfm?Story_ID=442930 on Jan. 25, 2001, 8 pages, Dec. 7, 2000.

Anderson, Rolfe C. et al., "Microfluidic Biochemical Analysis System," Transducers '97, 1997 International Conference on Solid-State Sensors and Actuators, Chicago, Illinois, pp. 477-480, Jun. 16-19, 1997.

Angell, James B. et al., "Silicon Micromechanical Devices," Scientific American, pp. cover, 44-55, Apr. 1983.

Armani, Deniz et al., "Re-Configurable Fluid Circuits By PDMS Elastomer Micromachining," IEEE Int. Conf. Micro Electro Mech. Syst. Tech. Digest, vol. 12, pp. 222-227, 1999.

Ashkin, A. et al., "Optical Trapping and Manipulation Of Single Cells Using Infrared Laser Beams," Nature, vol. 330, No. 24, pp. 769-771, Dec. 31, 1987.

Ashkin, A. et al., "Optical Trapping and Manipulation Of Viruses And Bacteria," Science, vol. 235, pp. 1517-1520, Mar. 20, 1987.

Ballantyne, J. P. et al., "Selective Area Metallization By Electron-Beam Controlled Direct Metallic Deposition," J. Vac. Sci. Technol., vol. 10, No. 6, pp. 1094-1097, Nov. 1973.

"Biochips," Nature Biotechnology, vol. 18, Supplement 2000, pp. IT43-IT44, 2000.

Bloomstein, T. M. et al., "Laser-Chemical Three-Dimensional Writing For Microelectromechanics And Application To Standard-Cell Microfluidics," J. Vac. Sci. Technol. B, vol. 10, No. 6, pp. 2671-2674, Nov. 1992.

Bousse, Luc et al., "Electrokinetically Controlled Microfluidic Analysis Systems," Annu. Rev. Biophys. Biomol. Struct., vol. 29, pp. 155-181, 2000.

Buican, Tudor N. et al., "Automated Single-Cell Manipulation And Sorting By Light Trapping," Applied Optics, vol. 26, No. 24, pp. 5311-5316, Dec. 15, 1987.

Burbaum, Jonathan J. et al., "New Technologies For High-Throughput Screening," Current Opinion in Chemical Biology, vol. 1, pp. 72-78, 1997.

Busch, J. et al., Methods For The Differentiation Of Microorganisms, Journal of Chromatography B. vol. 722, pp. 263-278, 1999.

Cai, Weiwen, et al., "High-Resolution Restriction Maps Of Bacterial Artificial Chromosomes Constructed By Optical Mapping," Proc. Natl. Acad. Sci. USA, vol. 95, pp. 3390-3395, Mar. 1998.

Calkins, Kathryn, "Mycometrix: Rubber Chips," BioCentury, 2 pages, Oct. 16, 2000.

Castro, Alonso et al., "Fluorescence Detection And Size Measurement Of Single DNA Molecules," Analytical Chemistry, vol. 85, No. 7, pp. 849-852, Apr. 1, 1993.

Chiu, Chi-Sung et al., "Single Molecule Measurements Calibrate Green Fluorescent Protein Surface Densities On Transparent Beads For Use With 'Knock-In' Animals And Other Expression Systems," Journal of Neuroscience Methods, vol. 105, pp. 55-63, 2001.

Chou, Hou-Pu et al., "A Microfabricated Rotary Pump," Biomedical Microdevices, vol. 3, No. 4, pp. 323-330, 2001.

Chou, Hou-Pu et al., "Disposable Microdevices For DNA Analysis And Cell Sorting," Proc. Solid-State Sensor and Actuator Workshop, Hilton Head, South Carolina, pp. 11-14, Jun. 8-11, 1998.

Chou, Hou-Pu et al., "Integrated Elastomer Fluidic Lab-On-A-Chip-Surface Patterning And DNA Diagnostics," Proceedings of the Solid State Actuator and Sensor Workshop, Hilton Head, South Carolina, 4 pages, 2000.

Chou, Hou-Pu et al., "Microfabricated Devices For Sizing DNA And Sorting Cells," Micro- and Nanofabricated Structures and Devices for Biomedical Environmental Applications, Proceedings of SPIE, vol. 3258, pp. 181-187, 1998.

Chou, Hou-Pu et al., "Multiple Disease Diagnostics On A Single Chip," Biophysics Lab, Caltech, pp. 1-4, Mar. 1, 2000.

"Electro Microfluidic Dual In-Line Package (EMDIP)," Sandia National Laboratories, 2 pages, no date, 2001.

Fettinger, J. C. et al., "Stacked Modules For Micro Flow Systems In Chemical Analysis: Concept And Studies Using An Enlarged Model," Sensors and Actuators B, vol. 17, pp. 19-25, 1993.

Fiedler, Stefan et al., "Dielectrophoretic Sorting Of Particles And Cells In A Microsystem," Analytical Chemistry, vol. 70, No. 9, pp. 1909-1915, May 1, 1998.

Folch, A. et al., "Molding Of Deep Polydimethylsiloxane Microstructures For Microfluidics And Biological Applications," Journal of Biomechanical Engineering, vol. 121, pp. 28-34, Feb. 1999.

Fulwyler, M. J., "Electronic Separation of Biological Cells By Volume," Science, pp. 910-911, Nov. 1965.

Galambos, Paul et al., "Electrical And Fluidic Packaging Of Surface Micromachined Electro-Microfluidic Devices," 3 pages, no date, Sep. 2000.

Gao, Jun et al., "Integrated Microfluidic System Enabling Protein Digestion, Peptide Separation, And Protein Identification," Analytical Chemistry, vol. 73, No. 11, pp. 2648-2655, Jun. 1, 2001.

Goodwin, Peter M. et al., "Rapid Sizing Of Individual Fluorescently Stained DNA Fragments By Flow Cytometry," Nucleic Acids Research, vol. 21, No. 4, pp. 803-806, 1993.

Greene, Chana, "Characterizing The Properties Of PDMS," pp. 1-11, Summer 2000.

Guérin, L. J. et al., "Simple And Low Cost Fabrication Of Embedded Micro-Channels By Using A New Thick-Film Photoplastic," Transducers '97, 1997 International Conference on Solid-State Sensors and Actuators, Chicago, Illinois, pp. 1419-1422, Jun. 18-19, 1997.

Henion, Jack et al., "Capilllary Electrophoresis/Mass Spectrometry: From One Meter Capillaries To Chip-Based Devices," 2 pages, 1999.

Hicks, Jennifer, "Genetics And Drug Discovery Dominate Microarray Research," R&D Magazine, pp. 28-33, Feb. 1999.

Hofmann, Oliver et al., "Modular Approach To Fabrication Of Three-Dimensional Microchannel Systems In PDMS—Application To Sheath Flow Microchips," Lab on a Chip, vol. 1, pp. 108-114, 2001.

Horn, Howard, "Lab Chips Sector: Microtechnologies Are Changing Healthcare And More," Life Sciences, pp. 19-21, Mar. 20, 2001.

Jo, Byung-Ho et al., "Fabrication Of Three-Dimensional Microfluidic Systems By Stacking Molded Polydimethylsiloxane (PDMS) Layers" SPIE, vol. 3877, pp. 222-229, Sep. 1999.

Jo, Byung-Ho et al., "Three-Dimensional Micro-Channel Fabrication In Polydimethylsiloxane (PDMS) Elastomer," Journal of Microelectromechanical Systems, vol. 9, No. 1, pp. 76-81, Mar. 2000.

Kagan, C. R., "Organic-Inorganic Hybrid Materials As Semiconducting Channels In Thin-Film Field-Effect Transistors," Science, vol. 286, pp. 945-947, Oct. 29, 1999.

Kapur, Ravi et al., "Fabrication And Selective Surface Modification Of 3-Dimensionally Textured Biomedical Polymers From Etched Silicon Substrates," Journal of Biomedical Materials Research, vol. 33, pp. 205-216, 1996.

Keller, Richard A. et al., "Single-Molecule Fluorescence Analysis In Solution," Applied Spectroscopy, vol. 50, No. 7, pp. 12A-30A, Jul. 1996.

Khoo, Melvin et al., "A Novel Micromachined Magnetic Membrane Microfluid Pump," pp. 1-4, no date, 2000.

Kim, Enoch et al., "Polymer Microstructures Formed By Moulding In Capillaries," Nature, vol. 376, pp. 581-584, Aug. 17, 1995.

Kirk-Othmer, "Concise Encyclopedia of Chemical Technology," John Wiley & Sons, 5 pages, no date, 2005, 5th edition.

Kumar. Amit et al., "Features Of Gold Having Micrometer To Centimeter Dimensions Can Be Formed Through A Combination Of Stamping With An Elastomeric Stamp And An Alkanethiol 'Ink' Followed By Chemical Etching," Appl. Phys. Lett., vol. 63, No. 14, pp. 2002-2004, Oct. 4, 1993.

Kumar, Amit et al., "Patterning Self-Assembled Monolayers: Applications In Materials Science," Langmuir, vol. 10, pp. 1498-1511, 1994.

Lagally, Eric T. et al., "Monolithic Integrated Microfluidic DNA Amplification And Capillary Electrophoresis Analysis System," Sensors and Actuators B, vol. 63, pp. 138-146, 2000.

Lagally, E. T. et al., "Single-Molecule DNA Amplification And Analysis In An Integrated Microfluidic Device," Analytical Chemistry, vol. 73, No. 3, pp. 565-570, Feb. 1, 2001.

Lammerink, T. S. J. et al., "Modular Concept For Fluid Handling Systems," IEEE, pp. 389-394, 1996.

Lessard, Guillaume A. et al., "A Scanning Apertureless Fluorescence Microscope," 8 pages, no date, 1999.

Licklider, Larry et al., "A Micromachined Chip-Based Electrospray Source For Mass Spectrometry," Analytical Chemistry, vol. 72, No. 2, pp. 367-375, Jan. 15, 2000.

Manz, A. et al., "Micromachining Of Monocrystalline Silicon And Glass For Chemical Analysis Systems," Trends in Analytical Chemistry, vol. 10, No. 5, pp. 144-149, 1991.

Marshall, SID, "Fundamental Changes Ahead For Lab Instrumentation," R&D Magazine, 5 pages, Feb. 1999.

Marsili, Ray, "Lab-On-A-Chip Poised To Revolutionize Sample Prep," R&D Magazine, 5 pages, Feb. 1999.

Maule, John, "Pulsed-Field Gel Electrophoresis," Molecular Biotechnology, vol. 9, pp. 107-126, 1998.

McDonald, J. Cooper et al., "Fabrication Of Microfluidic Systems In Poly(dimethylsiloxane)," Electrophoresis, vol. 21, pp. 27-40, 2000.

Melamed, Myron R. et al., "Flow Cytometry And Sorting," John Wiley & Sons, 32 pages, 1979.

Oleschuk, Richard D. et al., "Analytical Microdevices For Mass Spectrometry," Trends In Analytical Chemistry, vol. 19, No. 6., pp. 379-388, 2000.

O'Reilly, Marie-Anne J. et al., "The Technique Of Pulsed Field Gel Electrophoresis And Its Impact On Molecular Immunology," Journal of Immunological Methods, vol. 131, pp. 1-13, 1990.

Petty, Jeffrey T. et al., "Characterization Of DNA Size Determination Of Small Fragments By Flow Cytometry," Anal. Chem., vol. 67, pp. 1755-1761, 1995.

Samad, Akhtar et al., "Optical Mapping: A Novel, Single-Molecule Approach To Genomic Analysis," Genome Research, pp. 1-4, 1995.

Sanjoh, Akira et al., "Spatiotemporal Protein Crystal Growth Studies Using Microfluidic Silicon Devices," Journal of Crystal Growth, vol. 196, pp. 691-702, 1999.

Schwartz, David C. et al., "Optical Mapping Approaches To Molecular Genomics," Current Opinion in Biotechnology, vol. 8, pp. 70-74, 1997.

Sklar, Larry A. et al., Sample Handling For Kinetics And Molecular Assembly In Flow Cytometry, SPIE, vol. 3256, pp. 144-153, 1998.

Stemmer, Willem P. C. et al., "Rapid Evolution Of A Protein in vitro By DNA Shuffling," Nature, vol. 370, pp. 389-390, Aug. 4, 1994.

Sweet, Richard G., "Flow Sorters For Biologic Cells," pp. 177-189, no date, 1979.

Thompson, L. F. et al., "Introduction to Microlithography," 185th Meeting of the American Chemical Society, Seattle, WA, pp. 2 cover pages, 1-13, Mar. 20-25, 1983.

Thorsen, Todd et al., "Dynamic Pattern Formation In A Vesicle-Generating Microfluidic Device," Physical Review Letters, vol. 86, No. 18, pp. 4163-4166, Apr. 30, 2001.

Todd, Paul et al., "Cell Electrophoresis," pp. 217-229, no date, 1994.

Unger, Marc A. et al., "Single-Molecule Fluorescence Observed With Mercury Lamp Illumination," Biotechniques, vol. 27, No. 5, pp. 1008-1014, Nov. 1999.

Van Den Berg, A. et al., "Micro Total Analysis Systems," Proceedings of the µTAS '94 Workshop, University of Twente, The Netherlands, 17 pages, Nov. 21-22, 1994.

Verpoorte, Elisabeth M. J. et al., "Three-Dimensional Micro Flow Manifolds For Miniaturized Chemical Analysis Systems," J. Micromech. Microeng., vol. 7, pp. 246-256, 1994.

Volkmuth, W. D. et al., DNA Electrodiffusion In A 2D Array Of Posts, Physical Review Letters, vol. 72, No. 13, pp. 2117-2120, Mar. 28, 1994.

Volkmuth, W. D. et al., "DNA Electrophoresis In Microlithographic Arrays," Nature, vol. 358, pp. 600-601, Aug. 13, 1992.

Whitesides, George M. et al., "Flexible Methods For Microfluidics," Physics Today, pp. 42-48, Jun. 2001.

Whitesides, George M. et al., "Soft Lithography In Biology And Biochemistry," Annu. Rev. Biomed. Eng., vol. 3. pp. 335-373, 2001.

Wilbur, James L. et al., "Lithographic Molding: A Convenient Route To Structures With Sub-Micrometer Dimensions," Adv. Mater., vol. 7, No. 7, pp. 649-652, 1995.

Xia, Younan et al., "Reduction In The Size Of Features Of Patterned SAMs Generated By Microcontact Printing With Mechanical Compression Of The Stamp," Adv. Mater., vol. 7, No. 5, pp. 471-473, 1995.

Xu, Bing et al., "Making Negative Poisson's Ratio Microstructures By Soft Lithography," Adv. Mater., vol. 11, No. 14, pp. 1186-1189, 1999.

Yang, T. J. et al., "An Apertureless Near-Field Microscope For Fluorescence Imaging," Applied Physics Letters, vol. 76, No. 3, pp. 378-380, Jan. 17, 2000.

Yang, Xing et al., "A Lower Power MEMS Silicone/Parylene Valve," Solid-State Sensor and Actuator Workshop, Hilton Head Island, South Carolina, 4 pages, Jun. 7-11, 1998.

* cited by examiner

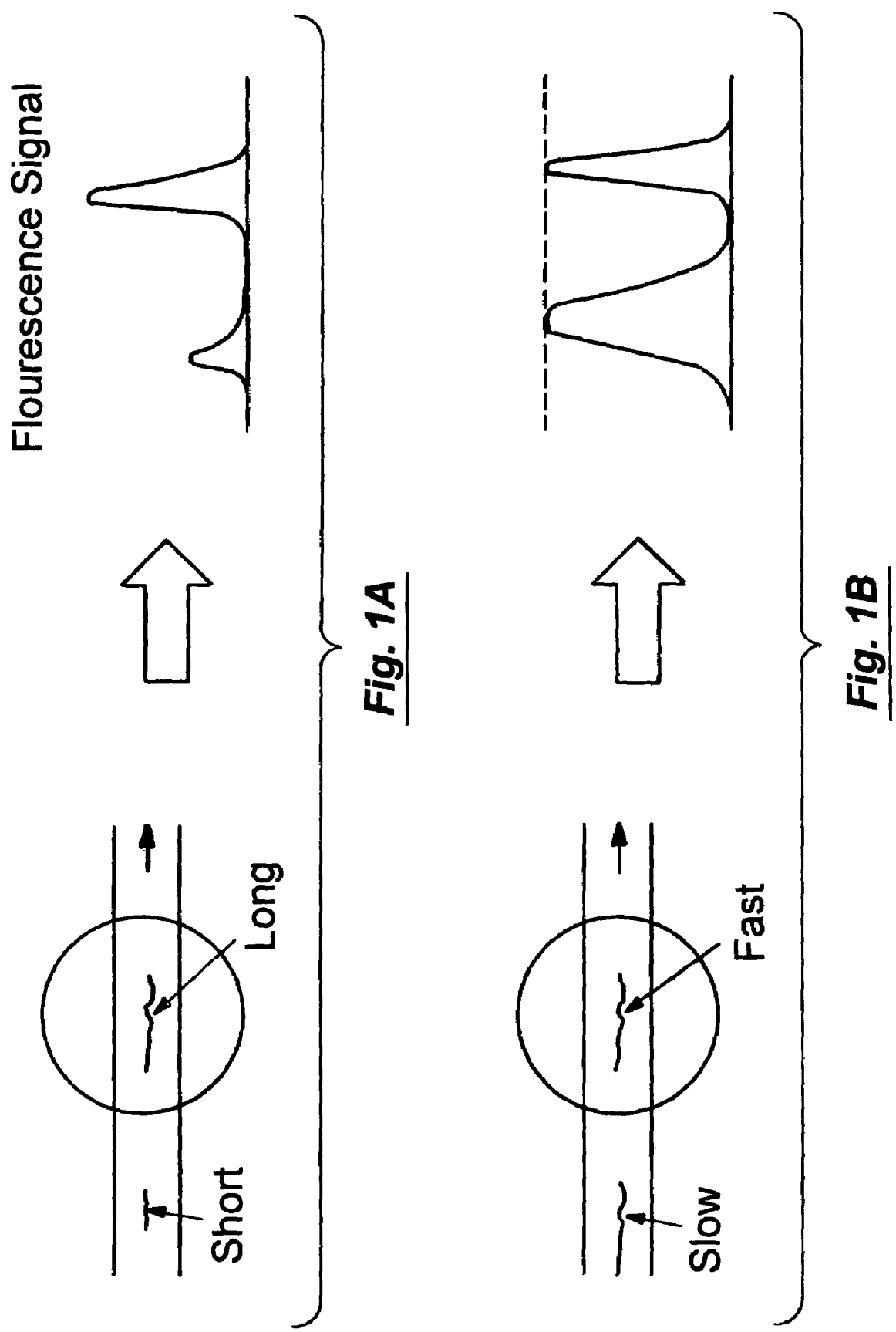

ArVlAnalyzer

Input: two files (one for each line scan).
     Each file contain 2 vectors one of Positions (P(i)) and the other has the corresponding Area (A(i))
Output: three vectors - Area, TimeDiff (inversely proportional to velocity), Position
Parameters that can be determined - MinTimeDiff, MaxTimeDiff

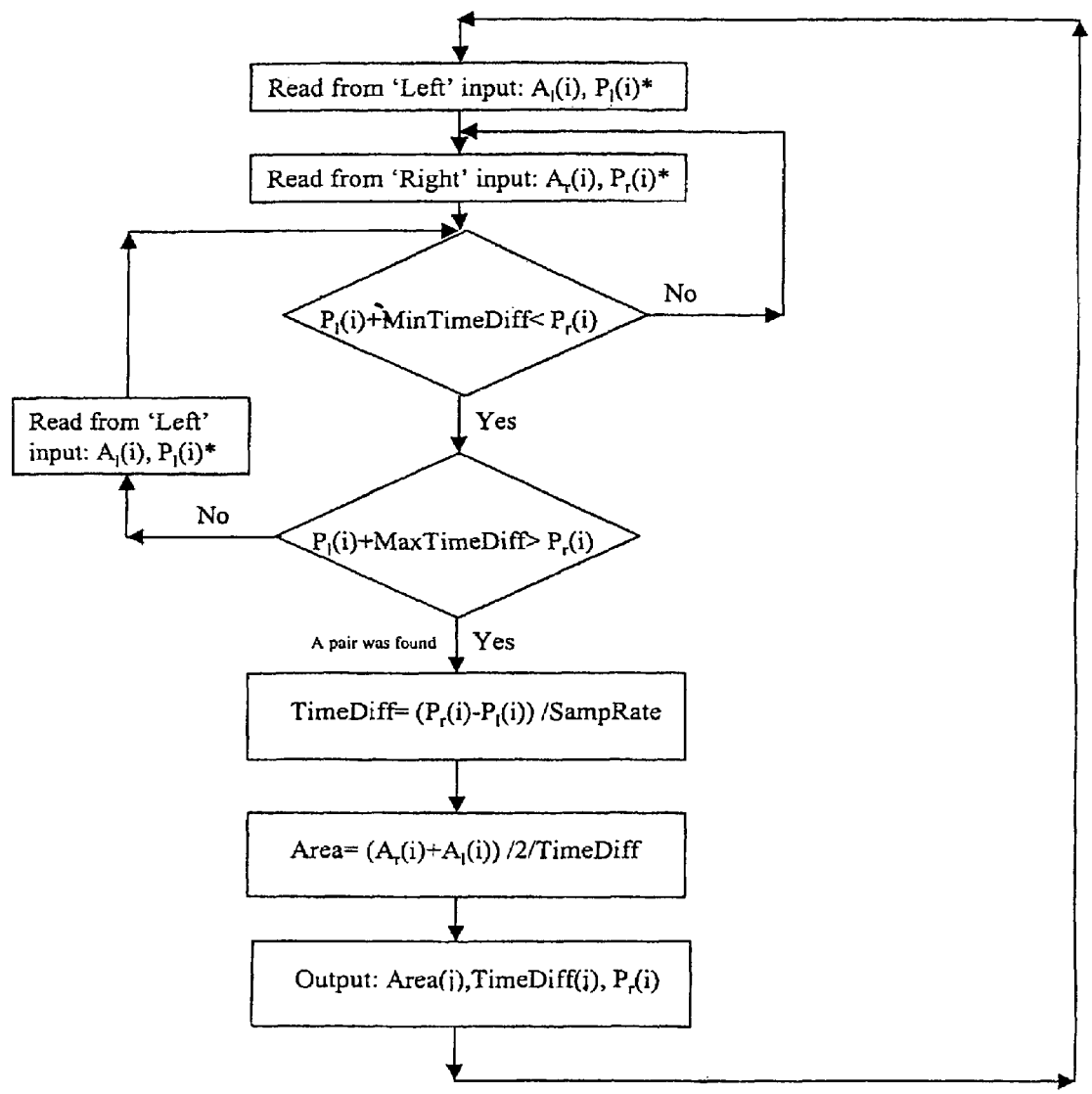

Position is presented in point number and not time
TimeDiff is in Seconds and is inversely proportional to the velocity
* Program ends when one of the input files ends

FIG. 8

VELOCITY INDEPENDENT ANALYTE CHARACTERIZATION

CROSS-REFERENCE TO RELATED APPLICATIONS

This application claims the benefit of U.S. Provisional Application No. 60/237,937, filed Oct. 3, 2000, which is incorporated herein by reference in it entirety.

STATEMENT REGARDING FEDERALLY SPONSORED RESEARCH

The U.S. Government has a paid-up license in this invention and the right in limited circumstances to require the patent owner to license others on reasonable terms as provided for by the terms of Grant No. HG-01642-02, awarded by the National Institute of Health.

FIELD OF THE INVENTION

The present invention relates to an apparatus and a method for determining a characteristic parameter of an analyte in a fluid medium. In one particular aspect, the present invention relates to a velocity independent flow cytometry.

BACKGROUND OF THE INVENTION

Recently, there has been a growing interest in microfluidic flow cytometry. Several chip based systems have been demonstrated for cytometry and sorting of cells and molecules. See, for example, Unger et al., *Science*, 2000, 288, 113-116; Fu et al., *Nature Biotechnol.*, 1999,17, 1109-1111; Quake et al., *Science*, 2000, 290, 1536-1540; Schrum et al., *Anal. Chem.*, 1999, 71, 4173-4177; Knight et al., *Phys Rev. Lett.*, 1998, 80, 3863-3866; Chou et al., *Proc. Natl. Acad. Sci. USA*, 1999, 96, 11-13; Chou et al., *Electrophoresis*, 2000, 21, 81-90; and Kameoka, et al., *Sensors and Actuators B*, 2001, 77, 632-637. There are generally two ways to pump fluid in these devices: pressure driven flow or by electroosmotic forces. Pressure driven flow results in Poiseulle flow, which has a parabolic velocity distribution in the channel. This complicates measurement of analytes since each analyte, e.g., cell or molecule, passes through the interrogation region with a different velocity. One can mitigate the effects of the Poiseulle flow by using a sheath fluid for hydrodynamic focusing, but this introduces other issues by diluting the sample and complicating downstream analysis. Although electroosmotic flow is typically more uniform and plug-like than pressure driven flow, it too results in variability in flow velocity. See, for example, Schrum et al., *Anal. Chem.*, 1999, 71, 4173-4177. In addition, most, if not all, electroosmostic flow requires careful balancing of the ions in the solution and attention to prevent ion depletion. Furthermore, in some cases, it has also been shown that eukaryotic cells are difficult to manipulate electroosmotically. See, for example, Li et al., *Anal. Chem.*, 1997, 69, 1564-1568.

One possible method for measuring a velocity independent characteristic parameter, e.g., fluorescence, of an analyte is to use a uniform detection zone, e.g., excitation region, large enough to illuminate the entire particle or molecule of interest. In this case, the height of the detected fluorescent peak will be substantially proportional to the fluorescence intensity of the particle. See, for example, Chou et al., *Proc. Natl. Acad. Sci. USA*, 1999, 96, 11-13. While this method is substantially not affected by the distribution of velocities, using only one point from the entire peak, namely its maximum, exploits only a small part of the information that is embedded in the peak. Moreover, the accuracy of this method is susceptible to noises. On the other hand, measuring the area underneath the entire peak, which is proportional to total fluorescence intensity integrated over the excitation duration, is velocity dependent measurement. This is due to the fact that faster particles have narrower peaks than slower particles. This will result in integrals being inversely proportional to the velocity of the particle. One solution is to normalize the area of each peak by the velocity of the corresponding particle to obtain velocity independent measurement of the fluorescence intensity.

Several methods for measuring the velocity in microfluidic devices have been reported. In particle image velocimetry, video imaging is used to measure the velocities of particles in a channel by observing the displacement of the particles within a known time interval. See, for example, Singh et al., *Anal. Chem.*, 2001, 73, 1057-1061; Barker et al., *Anal. Chem.*, 2000, 72, 5925-5929; and Santiago et al., *Experiments in Fluids*, 1998, 25, 316-319. This method is advantageous in obtaining the velocity spatial distribution, however it is not suitable for accurately measuring other analyte characteristic parameters, such as the fluorescent intensity.

Shah convolution Fourier transform is another method to measure velocity in microfluidic devices. See, for example, Kwok et al., *Anal. Chem.*, 2001, 73, 1748-1753 and Crabtree et al., *Anal. Chem.*, 1999, 71, 2130-2138. In this method, a mask with a periodic array of slits spatially modulates the excitation beam. When an analyte is moving in the beam the spatial modulation is converted into a temporal modulation. The distribution of velocities is found by Fourier transforming the temporal signal and identifying the peaks. However, such a practical use of this method has not been demonstrated. Moreover, the practical implementation of this method most likely will require fabrication of the mask on the chip which adds to the complexity of the device.

Therefore, there is a need for apparatuses and methods for determining a velocity independent analyte characteristic parameter.

SUMMARY OF THE INVENTION

One aspect of the present invention provides an apparatus for determining a characteristic parameter of an analyte in a fluid medium independent of the flow velocity of the analyte, said apparatus comprising:

(a) a device comprising a fluid flow channel;

(b) a means for transporting a fluid medium from a first position to a second position of the fluid flow channel;

(c) a plurality of detection zones located at different positions along said fluid flow channel and located in between the first and the second position of the fluid flow channel;

(d) a detector for detecting the analyte flowing through the detection zone; and (e) a means for measuring a characteristic parameter of the analyte independent of the flow velocity of the analyte through the plurality of detection zones.

Preferably, the device which comprises a fluid flow channel is a microfluidic device. While the fluid medium can be transported through the fluid flow channel by any conventional means, preferably means for transporting a fluid medium comprises a peristaltic pump or electroosmosis. More preferably, the microfluidic device comprises a peristaltic pump. Such microfluidic devices are particularly advantageous because the median fluid medium flow velocity can be controlled.

In one particular embodiment, the detector comprises a laser, a laser beam guiding device and a fluorescence measuring device. Preferably, the laser beam guiding device is an acousto-optic modulator. In this manner, a velocity independent integrated fluorescence peak area of the analyte can be detemined.

Another aspect of the present invention provides a method for determining a velocity independent characteristic parameter of an analyte, wherein the characteristic parameter of the analyte is capable of being influenced by or dependent on the velocity of the analyte, said method comprising:

(a) providing a means for transporting a fluid medium comprising the analyte from a first position to a second position of a fluid flow channel of a fluidic device;

(b) measuring the characteristic parameter of the analyte within the fluid flow channel at a plurality of locations along the fluid flow channel in between the first and the second position; and (c) determining the velocity independent characteristic parameter of the analyte using the measured characteristic parameters of step (b) and normalizing the measurement by substantially eliminating the velocity component of the measurement.

The velocity independent characteristic parameter of the analyte can be determined by:

(i) comparing signals obtained from the plurality of locations along the fluid flow channel in step (b);

(ii) determining a time difference by calculating the time it takes for a particular analyte to pass from a first detection position to a second detection position; and (iii) determining the velocity independent characteristic parameter using the time difference.

Preferably, the signals from the first and the second detection zones are averaged and normalized using the time difference. By averaging the signals from the two detection zones, the amount of noise and false signals are significantly reduced by the methods of the present invention.

Apparatuses and methods of the present invention can be used in a variety of assay and analytical applications. In one particular embodiment, methods of the present invention provide cell sorting. Yet in another embodiment, methods of the present invention provide determining number of nucleotides present in an oligonucleotide. Such methods for determining the number of nucleotides in an oligonucleotide comprise:

(A) attaching a fluorescent molecule to the oligonucleotide to produce a modified oligonucleotide prior to measuring velocity independent characteristic parameter of the modified oligonucleotide, wherein said characteristic parameter is integrated fluorescent peak area of said modified oligonucleotide; and (B) determining the number of nucleotides in the oligonucleotide by comparing the velocity independent integrated fluorescence peak area of the modified oligonucleotide with a velocity independent fluorescence peak area of a standard oligonucleotide, wherein the velocity independent fluorescence peak area of the standard oligonucleotide has been calibrated to the number of nucleotides present the standard oligonucleotide.

BRIEF DESCRIPTION OF THE INVENTION

FIG. 1A is a fluorescence signal illustration showing that at a similar flow velocity the peak intensity and the peak area is proportional to the length of the DNA being detected by flow cytometry.

FIG. 1B is a fluorescence signal illustration showing peak areas of two similar length DNAs with different flow velocity.

FIG. 8 shows a flow chart of a computer program for determining a velocity independent flow cytometry.

DEFINITIONS

Figure 2A:
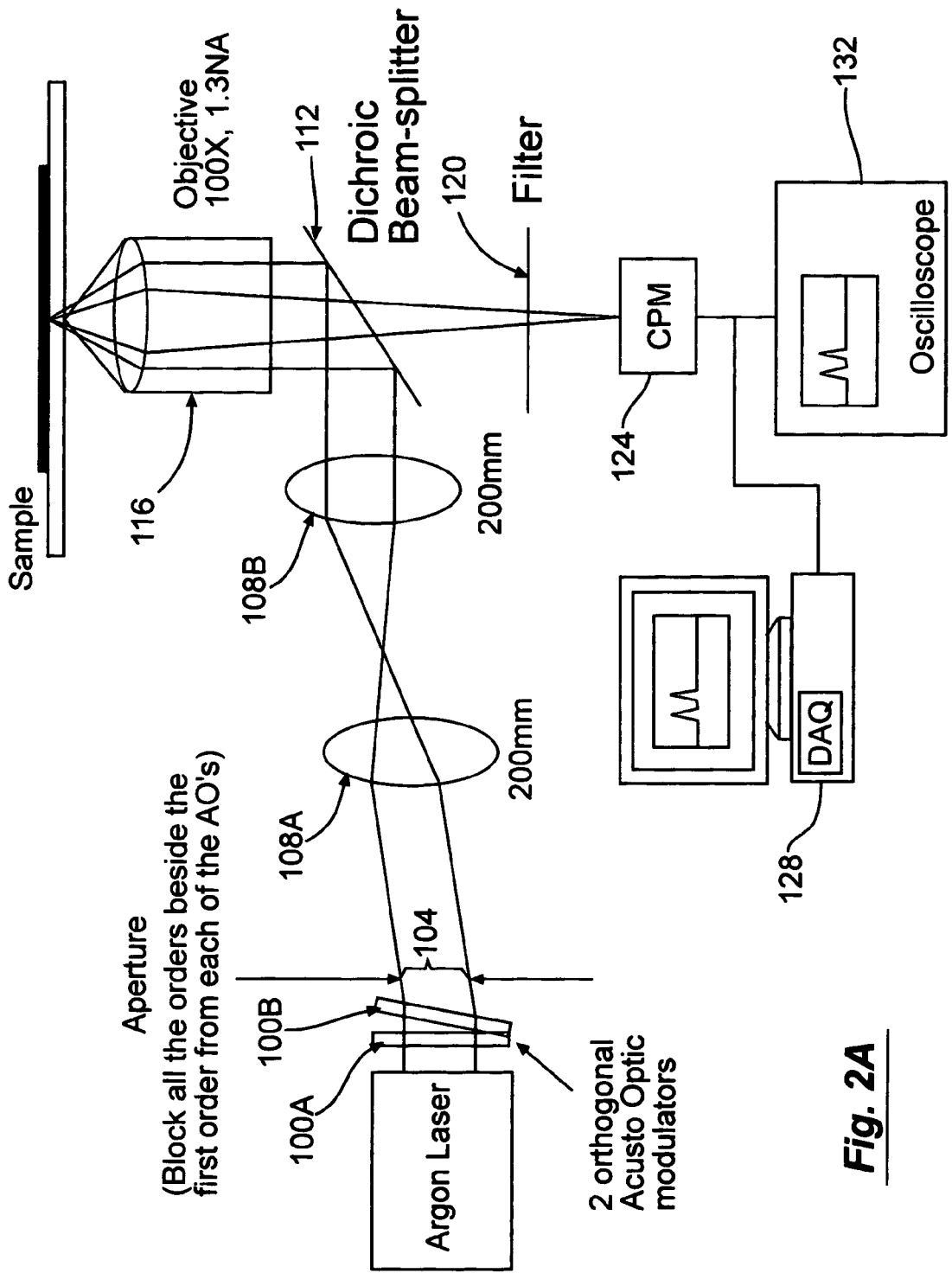
FIG. 2A shows a schematic illustration of an apparatus of the present invention.

"Analyte" refers to any material in a fluid medium which can be analyzed using a detector. Exemplary analytes include cells; oligonucleotides, such as DNA, RNA and PNAs; other organic compounds, such as pharmaceutically active compounds including antibiotics, antiviral compounds, anticancer compounds, etc.; beads; resins; polymers; and the like.

The terms "character of an analyte," "character parameter of an analyte" and "an analyte's characteristic" are used interchangeably herein and refer to a physical or chemical characteristic parameter of the analyte. Exemplary analyte's characteristics include molecular size (e.g., weight or length), fluorescence, infrared or UV/VIS absorption, nuclear magnetic resonance (i.e., NMR) spectrum, cell type, and other characteristics which can be measured or detected by a suitable detector known to one skilled in the art.

The terms "fluid" and "fluid medium" are used interchangeably herein and refer to a gas, or preferably liquid.

The terms "velocity" and "flow velocity" when referring to an analyte are used interchangeably herein and refer to the flow velocity of the analyte within a fluid medium.

DESCRIPTION OF THE SPECIFIC EMBODIMENTS

The present invention provides an apparatus for determining a plurality of characteristic parameters of an analyte in a fluid medium. In particular, the apparatus of the present invention allows determination of an analyte characteristic parameter and the analyte flow velocity within a fluid flow channel of a device. Preferably, the analyte characteristic parameter is capable of being influenced and/or affected by the analyte flow velocity. In this manner, the apparatus of the present invention provides or can be used to determine a velocity independent analyte characteristic parameter.

The analyte characteristic parameter can be any physical or chemical parameter that can be measured or determined using conventional detecting means. Suitable analyte characteristic parameters include UV/VIS absorption, fluorescence, nuclear magnetic resonance, infrared spectrum, and other physical or chemical parameters which can be measured as an integrated area under a peak or a curve. For the sake of brevity and clarity, the present invention will now be described in reference to measuring fluorescence of the analyte. Of course in order to measure fluorescence, the analyte must be capable of fluorescing when exposed to an appropriate electromagnetic radiation, e.g., ultraviolet and/or visible light. Thus, in one aspect the analyte comprises a fluorescent moiety.

The total fluorescence intensity integrated over the excitation duration is velocity dependent measurement. As expected, when fluorescence of analytes is measured in a narrow detection zone (i.e., area), analytes with faster flow velocity spend a relatively small amount of time within the detection zone resulting in a relatively smaller fluorescence intensity peak width compared to slower analytes. For example, as illustrated in FIG. 1A, at a similar velocity the peak intensity and the peak area is proportional to the length of the DNA being detected by flow cytometry. However, as shown in FIG. 1B, if two similar length of DNAs have different velocity, the faster moving DNA will have smaller peak area (in FIG. 1B, the dotted line shows that the peak heights of both particles are the same) and the slower moving DNA will have larger peak area. This velocity difference can lead to misleading or erroneous interpretation flow cytometry data.

The apparatuses and methods of the present invention significantly reduce or eliminate the affect of molecule velocity through a detection zone on the peak area by eliminating or normalizing the velocity factor of the analyte characteristic parameter. In particular, apparatuses of the present invention comprise at least two different detection zones along the analyte's flow path (i.e., fluid flow channel) to determine the velocity of each analyte that flows through the detection zones. By placing two different detection zones at a predetermined distance (i.e., "d") from each other, one can measure the velocity of the analyte flowing through the detection zones by measuring the time difference (i.e., "t") at which the analyte passes through the first detection zone and the second detection zone. Since the velocity (i.e., "v") is distance divided by time, the flow velocity of analyte is calculated by the formula: v=d/t, where v, d and t are those defined above. The peak area is then multiplied by the velocity (or simply divided by time since d is constant) to normalize the peaks, i.e., to eliminate the velocity factor. In this manner, a more accurate determination of the analyte characteristic parameter can be made.

Preferably, each analyte passes through the detection zone individually, i.e., separately. Therefore, the variables such as flow channel width, concentration of the analyte, and other variables which can affect the number of analyte passing through the detection zone is adjusted such that a single analyte flows through the detection zone at any given time. For measuring characteristic parameters of cells, the width of fluid flow channel is preferably in the order of from about 1 µm to about 1000 µm, more preferably from about 10 µm to about 100 µm, and still more preferably from about 5 µm to about 50 µm.

For example, for measuring characteristic parameters of a relatively large molecules having molecular weight of upto about a few hundred MDaltons, such as oligonucleotides including DNAs, RNAs, PNAs and hybrids thereof (having upto about few hundred base pairs); peptides; polymers; and other organic compounds, the width of the fluid flow channel is preferably in the range of from about 1 µm to about 50 µm, and more preferably from about 3 µm to about 10 µm. While the above fluid flow channel width are provided as being particularly suitable for certain analytes, it should be appreciated that other fluid flow channel widths are also within the scope of the present invention.

Devices comprising such fluid flow channel dimensions are well known to one skilled in the art. For example, any microfluidic devices currently known to one of ordinary skill in the art can be used in the present invention. However, preferred microfluidic devices are constructed of single or multilayer soft lithography (MLSL) as described by Unger et al. in *Science*, 2000, 288, 113-116, and further detailed in commonly assigned U.S. patent application Ser. No. 09/605,520, filed Jun. 27, 2000, which are incorporated herein by reference in their entirety. Other preferred microfluidic devices are disclosed in a commonly assigned U.S. Patent Application entitled "Microfluidic Devices and Methods of Use," which is filed even date with the present application and is further identified by attorney docket No. 020174-002510US, and is incorporated herein by reference in its entirety. Moreover, specific examples of microfluidic flow cytometry for sorting cells and DNA's are disclosed in commonly assigned U.S. patent application Ser. No. 09/325,667 and the corresponding published PCT Patent Application No. US99/13050, and U.S. patent application Ser. No. 09/499,943, respectively, all of which are incorporated herein by reference in their entirety.

While one can use multiple detectors and electromagnetic radiation sources (e.g., laser for laser induced fluorescence), it has been found by the present inventors that one or more, preferably two, acousto-optic modulators in conjunction with an aperture is particularly suitable for providing two different detection zones from a single laser source. An acousto-optic modulator is readily available from a variety of sources including Brimrose Corp. Baltimore, Md., which also provides documents with a general discussion on the theory behind acousto-optic modulators. Other devices which is capable of guiding the laser beam into two or more different positions can also be used instead of an acousto-optic modulator. Such devices are well known to one of ordinary skill in the art and include rotating mirrors, gratings and other electromagnetic wave diffracting devices. The aperture allows emission of only one particular diffracted beam to illuminate the detection zones and blocks other diffracted laser beam.

When using an acousto-optic modulator, preferably the first order beam is used. Thus, when two acousto-optic modulators are used, one to control direction of the laser beam in the x-axis and the other to control direction of the laser beam in the y-axis, the resulting laser beam is about 20% intensity of the original laser beam. This is because a typical first order laser beam intensity exiting an acousto-optic modulator is about 50% of the laser beam entering it. Therefore, by using two acousto-optic modulator, the resulting laser beam is about 20% to about 30% intensity of the original laser beam.

As stated above, an aperture is typically used in conjunction with acousto-optic modulators. The aperture is used to select the first order laser beam from each of the acousto-optic modulators. For example, as shown in FIG. 2C, there are variety orders of diffracted laser beam resulting form two acousto-optic modulators. The aperture allows laser beam from only the first order of both acousto-optic modulator (i.e., 50) to be focused onto the detection zones.

A typical set-up for using a laser to detect fluorescence of the analyte in two detection zones is schematically illustrated in FIG. 2A. The laser beam enters two orthogonally located acousto-optic modulators 100A and 100B. The aperture 104 then allows only the first order laser beam from both of the acousto-optic modulators to pass through. The resulting laser beam then passes through two lenses 108A and 108B. However, the use of two lenses is optional and can be omitted.

Typically, the lenses are used to adjust the distance between the two scan lines (i.e., detection zones) as well as their length, for example, to be in the order of about 10 µm.

The laser beam is then deflects off the dichroic beam-splitter 112 and is focused on to the detection zones through an objective 116. The fluorescence wavelength then passes through a filter 120 to a channel photo-multiplier 124, which is operatively interconnected to a data acquisition device 128. The optional oscilloscope 132 can be used to observe the signal prior to data acquisition and/or to observe the signal in real-time.

Figure 2B:
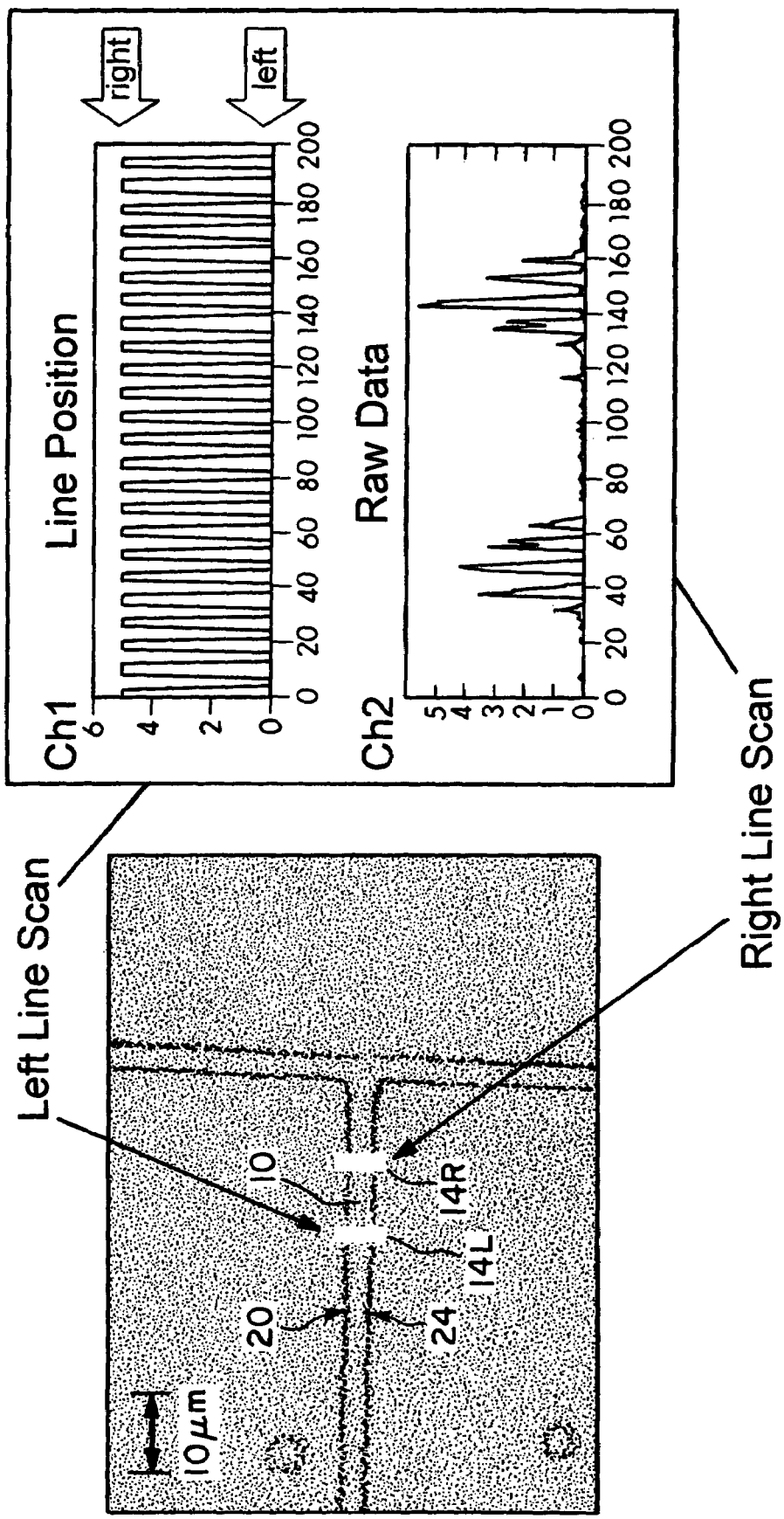
FIG. 2B shows CCD camera image of fluorescein solution flowing through a T-channel of a microfluidic device illuminated by the scanning beam and two-dimensional laser beam scanning by acousto-optic modulator and the corresponding square wave (top, i.e., Ch1) and fluorescence data (bottom, i.e., Ch2).
Figure 2C:
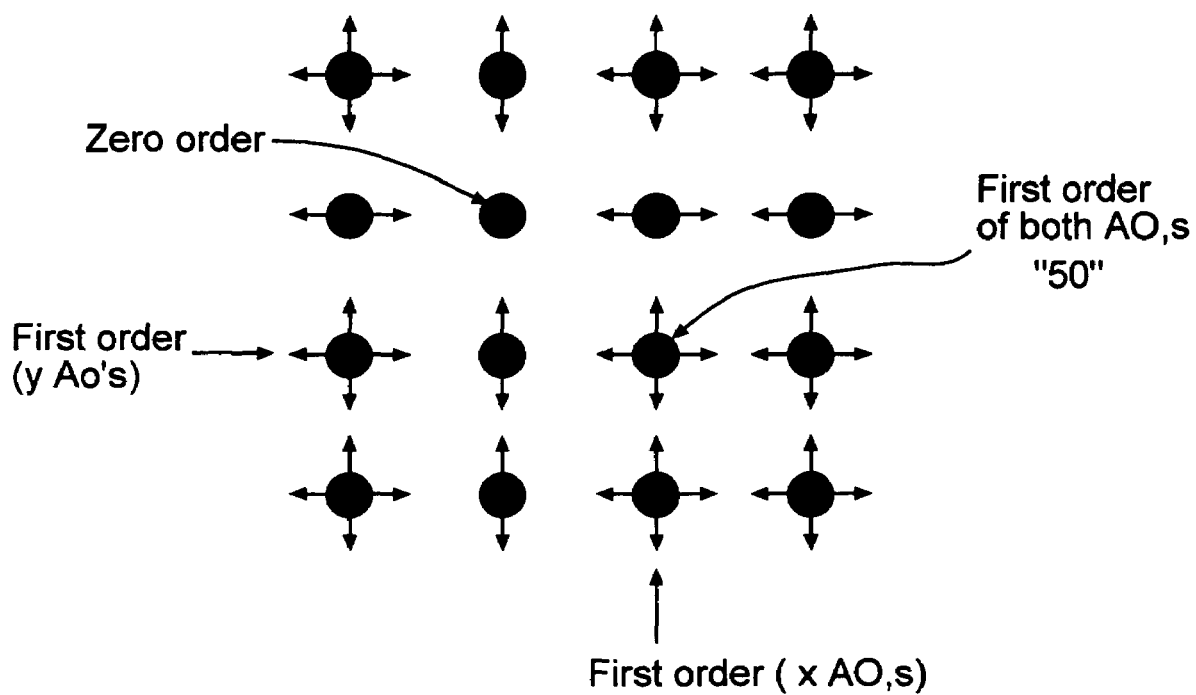
FIG. 2C illustrates a laser beam location and the order after passing through two orthogonally located acousto-optic modulators.

The result of one particular embodiment of the present invention is shown in FIG. 2B. The left portion of FIG. 2B shows a T-shaped flow channel which is illuminated with fluorescence at two different detection zone of the flow channel. The right portion of FIG. 2B shows signal peaks corresponding to the square wave which controls the x-axis position, i.e., the detection zone, of the laser beam and the fluorescence peaks obtained from the two detection zones. In this embodiment, the distance 10 between the two detection zones 14L and 14R is about 10 µm and the width of the fluid flow channel is about 5 µm. The laser beam enters two orthogonally positioned acousto-optic modulators 100A and 100B and the resulting first order beam is emitted through an aperture 104. In order to scan the entire cross section of the fluid flow channel and to allow scan of two different detection zones 14L and 14R, two acousto optic modulators are used. One to control the x-axis and the other to control the y-axis of the laser beam. In FIG. 2B, the beam has y-axis frequency of 150 kHz, i.e., the beam travels from above the "top" of the flow channel 20 to below the "bottom" of the flow channel 24 at a rate of 150,000 times per second. In actuality the beam scans twice the distance relative to the width of the fluid flow channel; however, because there is no fluorescence outside the fluid flow channel, no beam is visible outside the fluid flow channel in FIG. 2B. Furthermore, the laser beam switches from the detection zone 14L to 14R and vice a versa at a rate of 5 kHz. In addition, the laser beam has a sampling rate of 40 kHz, i.e., each x-position is sampled about 4 times or 8 times total (40/5). Frequency of x-axis switching can be seen in the top graph of the right portion of FIG. 2B. In this graph, when the peak is at the top, it represents detection (or scanning) in the 14R region, and when the peak is at the bottom (i.e., 0) it represents detection (or scanning) in the 14L region. As can be seen, the laser beam moves from one position to another (in the x-axis) to allow scanning of two different positions. This allows the same analyte to be detected at two different times at two different regions as shown in the lower graph of the right portion of FIG. 2B. By determining the time difference between such detection and knowing the distance 10 (FIG. 2A), one can calculate the velocity of the material traveling through the fluid flow channel. As stated above, it is preferred that statistically each analyte enters the detection zone separately.

As stated above, the left portion of FIG. 2B illustrates scanning two detection zones of a T-shaped fluid flow channel by the scanning beam. A fluid medium comprising fluorescein was introduced to the fluid flow channel and was excited by the scanning beam in two scan lines as shown. The resulting fluorescence was imaged with a CCD camera as shown in FIG. 2B. The two scan lines are clearly visible. It is important to note that the two scan lines can be seen together only due to the limited time resolution of the CCD compared to the scanning frequency. In actuality, the two bright lines of FIG. 2B are actually fluorescing at different times. The lines scanned by the illuminating beams are about two times longer than the bright lines shown in FIG. 2B to ensure uniform excitation of the region of interest. However, the full line can not be seen because there is no fluorescein outside of the fluid flow channels, and therefore no fluorescence occurs there. The width of the fluid flow channel in FIG. 2B is 5 µm and its depth is 3.9 µm.

As shown in FIG. 2A, in one embodiment the laser beam is transmitted through two mutually orthogonal acousto-optic (AO) modulators, represented as items 100A and 100B, to produce two line scans. Each AO was driven by voltage controlled oscillator (VCO) connected to a function generator (not shown), such as Stanford Research Systems, Model DS335 (Sunnyvale, Calif.). As implied above, one of the AO is used to move the beam in the x direction, i.e., parallel to the direction of the fluid flow. Typically, this VCO was driven with a square wave (e.g., 5 KHz, $7V_{p-p}$) thereby allowing one to scan two different detection zones along the fluid flow channel. Because the laser beam scans only a small fraction of the width of the fluid flow channel, a second AO is required to scan the entire width of the fluid flow channel. This second AO is preferably oriented to enable the laser beam to move in the Y direction, thus allowing the beam to cross the entire width of the fluid flow channel. Typically, the signal for controlling this second AO is a sinusoidal wave (e.g., 120 KHz, $9V_{p-p}$) at a frequency higher than the chopping signal to ensure several crossing of the channel for each position on the x direction. At the exit of the second AO the original laser beam is divided into a grid of beams as illustrated in FIG. 2C. Most of these beams are blocked using an aperture 104 leaving only the beam that is the combination of the first orders of both AOs. This beam is then used to scan along two parallel lines (left and right line scans) in different positions along the fluid flow. Such scanning can be conveniently accomplished by a VCO. As stated above, the data acquisition can be conveniently accomplished by a channel photo-multiplier 124 operatively connected to a data acquisition device, such as a computer 128 or other signal recording device, including a plotter. Typically, the two signals, the square wave used to control AOs and the fluorescence signal, are recorded separately, i.e., as Ch1 and Ch2 in FIG. 2B. By correlating signals of Ch2 to the square wave of Ch1 allows one to determine which peaks in Ch2 are from the left (14L) detection zone and which peaks are from the right (14R) detection zone.

Figure 3:
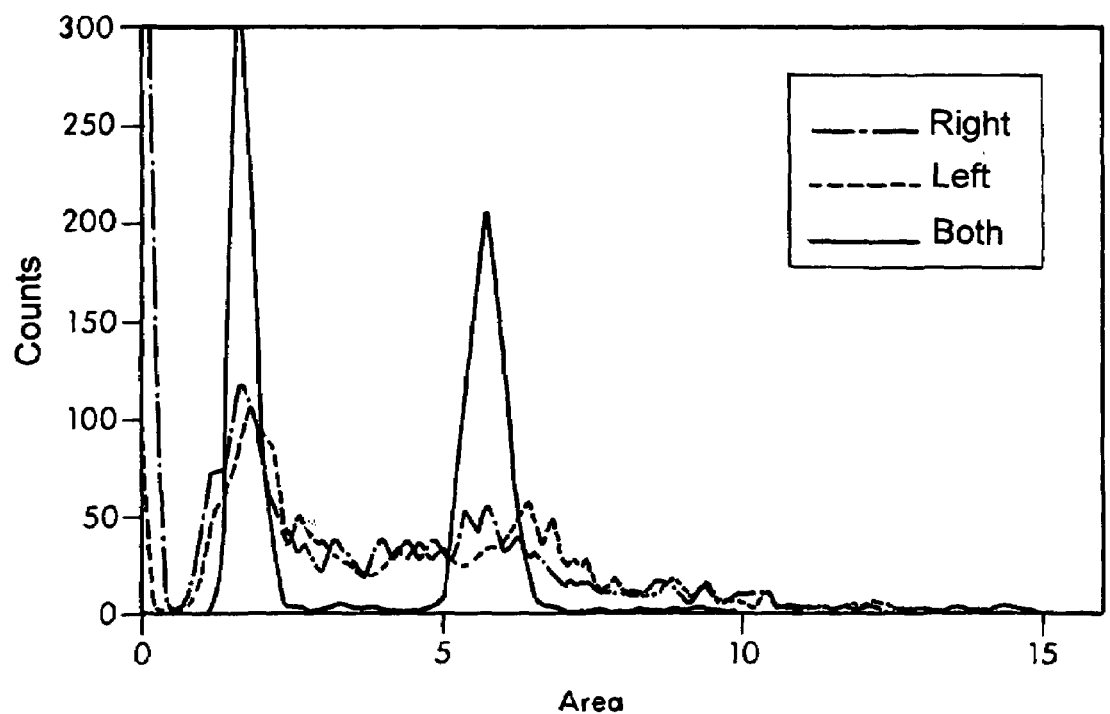
FIG. 3 shows histogram of the areas obtained from the fluorescence of two kinds of fluorescence beads with and without velocity normalization.

FIG. 3 is a histogram of the peak areas for 14L and 14R regions, as well as normalized, i.e., velocity independent, peak areas for an experiment conducted with two kinds of beads which differ in their fluorescent intensity. It is expected that the ideal histogram will have two peaks, one for each kind of beads. As the legends in FIG. 3 shows, the graph represents none normalized fluorescence peak areas from the left (14L) and right (14R) detection zones and a normalized, i.e., velocity independent, peaks (labeled as "both"). It has been found that in some cases averaging the normalized peak areas can reduce the coefficient of variance relative to using only a single detection zone.

It has been found by the present inventors that because apparatuses of the present invention provide a plurality of detection zones, the resulting peak area (i.e., characteristic parameter) that has been normalized have a significantly lower coefficient of variance compared to conventional apparatuses having only one detection zone. Typically, apparatuses and methods of the present invention improves the coefficient of variance by a factor of at least about 2 relative to a similarly equipped apparatus having only one detection zone, and preferably by a factor of at least about 3.

Gel-electrophoresis (i.e., electrophoresis) and other similar methods have limited resolution capacity for medium to large DNA molecules, and therefore are inapplicable in many cases. In contrast, apparatuses and methods of the present invention are not limited by the size of material (e.g., DNA). Moreover, if the distance between two detection zones are large or the velocity of the material is slow, one can use these variations to study a variety of analyte characteristic parameters. For example, one can detect changes in cells as it passes through from one detector to another. One can also analyze chromosome distribution in cells (e.g., karyotyping). Methods of the present invention are also useful in epidemiology and other diagnostic and assay procedures.

In one particular aspect, apparatuses of the present invention can be used to determine the size (e.g., number of base pairs) of oligonucleotides such as DNAs, RNAs, PNAs and hybrids thereof. For example, a calibration chart can be prepared by measuring fluorescence of oligonucleotides of a variety of lengths. To be useful, each oligonucleotides are coupled to a compound that is capable of fluorescing. The fluorescence compound is then coupled to the oligonucleotide at a regular interval, e.g., every four or five base pairs. The oligonucleotide of unknown length is then coupled to the same fluorescence compound at the same nucleotide interval. By measuring the fluorescence peak area and comparing the result with the calibration chart, e.g., by a computer, one can easily determine the length of the unknown oligonucleotide. Thus, apparatuses and methods of the present invention can be used as an alternative to electrophoresis to determine the size of oligonucleotides. However, unlike electrophoresis, apparatuses and methods of the present invention are generally not limited by the size of the oligonucleotide.

Apparatuses and methods of the present invention allow determination of analyte flow velocity and other characteristic parameter(s) of the analyte. For example, such apparatuses and method can be used to perform flow cytometry and determine the analyte flow velocity; thereby, enabling correlation of the velocity with each specific analyte. In addition, usefulness of apparatuses of the present invention is not limited by the size of the analyte. In contrast, measuring the fluorescence from the peak heights using a conventional apparatus typically requires the entire particle (i.e., analyte) to be uniformly illuminated by the excitation beam, thereby limiting the size of the particle which can be analyzed.

Data Acquisition and Analysis

In one particular embodiment of the present invention, the data acquisition involves scanning two different detection zones along the path of the fluid flow channel by AOs which are operatively interconnected to VCOs. Each detection zone is scanned at least the entire width of the fluid flow channel. Typically, each acquisition involves ten or more scans per detection zone. That is, the laser beam scans "up and down" the width of the detection zone (i.e., y-axis of the fluid flow channel) ten or more times before the x-axis position (i.e., detection zone) of the beam is switched. Data acquisition typically involves recording the fluorescence signal in each of the two detection zones and separately recording the square wave that is used to direct the laser beam from to different detection zones. If the peak and the valley of the square wave represent relative values 1 and 0, respectively, typically 0.05 and 0.95 fractions of square wave signals are used as the locations for the first and the second detection zones. This eliminates any noise factor that may be present in the signal, e.g., due to signal spikes.

As stated above, data acquisition involves recording the square wave frequency and the fluorescence intensity of the analyte. By correlating the square wave to the fluorescence peaks, one can determine whether a particular fluorescence peak is from the first or the second detection zone. For example, if the laser beam is directed at the first detection zone while the square wave is near its peak value, then any fluorescence peaks occurring at the same time as the peak of the square wave is due to fluorescence at the first detection zone. Conversely, any fluorescence peaks occurring while the square wave is near its bottom is due to fluorescence at the second detection zone. In this manner, the fluorescence signal can be separated into its two origin signals (one for each detection zone) even in cases where a particle is long enough to be in both detection zones at the same time. This type of data analysis algorithm allows detection of fluorescence from both detection zones using a single detector.

After each peak from the first detection zone has been correlated to a corresponding peak from the second detection zone, the peaks are then normalized by dividing the integrated peak area with the analyte flow velocity. The analyte flow velocity can be determined by the time difference between the positions of the two corresponding peaks. Since the distance between the first and the second detection zone is constant, the integrated peak area can be simply divided by the time it take for the analyte to travel from the first detection zone to the second detection zone. Because each integrated peak area from the first detection zone is correlated to the corresponding integrated peak area from the second detection zone, any integrated peak area from the first detection zone that does not have a corresponding integrated peak area in the second detection zone or vice a versa is most likely due to noise and is discarded. Thus, apparatuses and methods of the present invention provide more accurate analyte characteristic parameter determination than conventional single detection methods.

The distance between the two detection zones should be sufficiently large enough to allow accurate velocity determination, i.e., time it takes for the analyte to travel from the first detection zone to the second detection zone. Generally, the accuracy of the velocity determination is somewhat dependent on separation (in time or more importantly in sampling points) between the two corresponding fluorescence peaks. Therefore, larger separation of the fluorescence peaks, i.e., longer it take for an analyte to travel from the first detection zone to the second detection zone, results in more accurate velocity determination.

In one particularly preferred embodiment, statistically only one analyte passes through both detection zones before the second particle enters the first detection zone. In this manner, the integrated peak areas from the first detection zone can be readily correlated to the integrated peak areas from the second detection zone. This can be accomplished by adjusting one or both of the distance between two detection zones and the concentration of the analyte in the fluid medium. Of course these two parameters are also dependent on other variables such as the mean flow velocity of the fluid medium within the fluid flow channel and the square wave frequency (i.e., frequency at which the laser beam switches to and from the first and the second detection zones).

For example, for a mean fluid medium flow velocity of about 2 µm/sec and square wave frequency of 5000 $\sec^{-1}$, the distance between the two detection zone is about 10 µm. And the concentration of the analyte is typically from about 2 nM or less, preferably from about 0.2 nM to about 2 nM.

Theoretically, activating data acquisition prior to having any of the analyte pass through the first detection zone allows one to easily correlate each fluorescence peak to a particular particle, becasue the order of each peak on the first and the second detection zones will be equal to the order of particles passing through each detection zone. However, in many instances such signal acquisition is not feasible or practical.

Moreover, possible noises in each of the detection zones will prevent correlating the peak from one detection zone to another detection zone. Therefore, one needs to correlate the integrated peak area (e.g., fluorescence peaks) from the first detection zone to the corresponding integrated peak area of the second detection zone.

Figure 7:
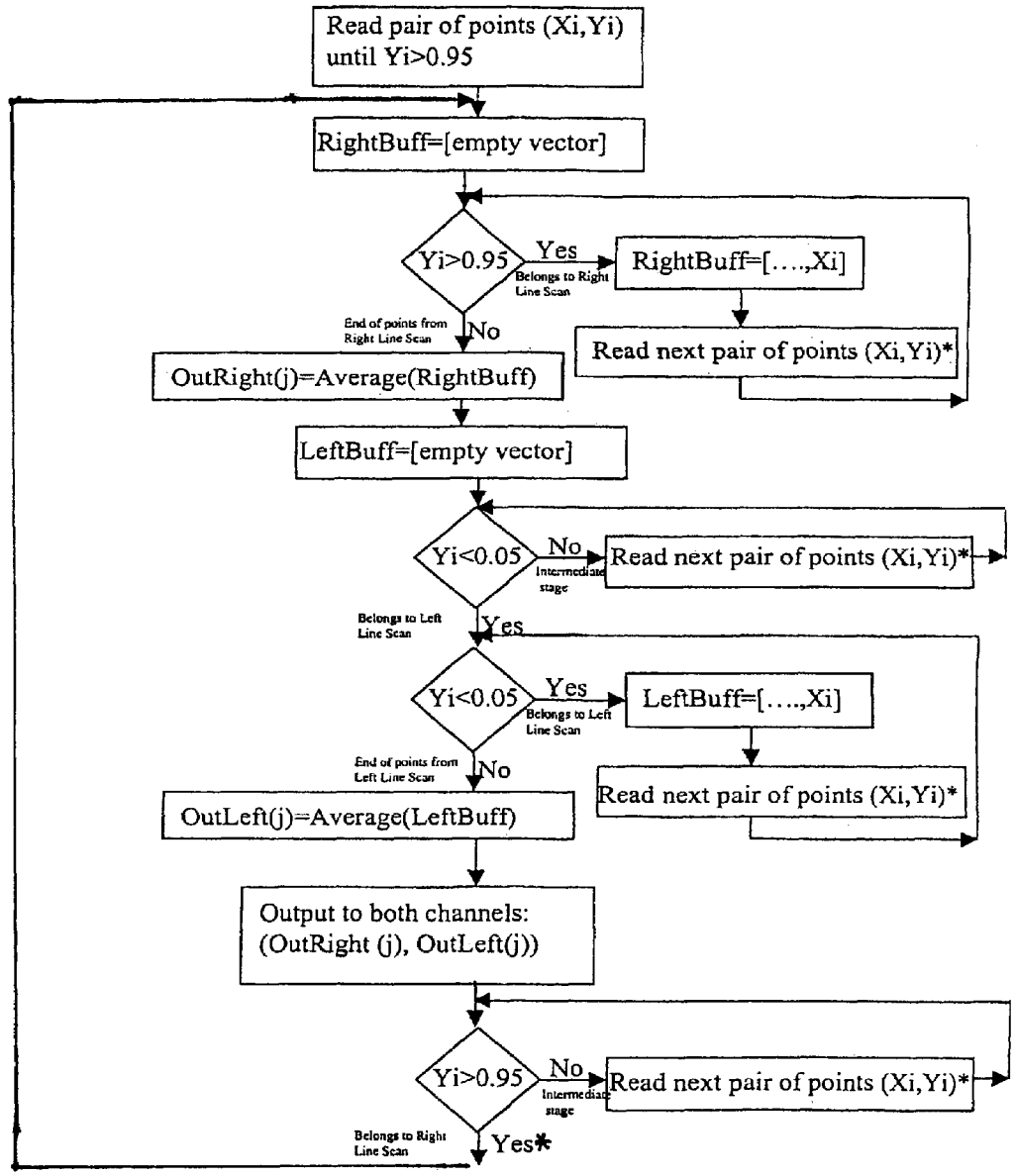
FIG. 7 shows a flow chart of a computer program for recording square waves and fluorescent peak data.

One method of achieving this correlation is to correlate the integrated peak area from the first detection zone to a corresponding integrated peak area in the second detection zone by limiting the detection to region of velocities about ±4 times the median flow velocity of the fluid medium. For example, integrated peaks from the first detection zone is compared to integrated peaks from the second detection zones in the range of ¼ the median flow velocity to 4× the median flow velocity of the fluid medium. By comparing other integrated peak areas of similar intervals, one can verify whether the initial correlation is accurate. Such a method for detecting and correlating the integrated peak areas from the first detection zone to the integrated peak areas of the second detection zone is schematically outlined in the flow sheets in FIGS. 7 and 8. Briefly, the two integrated peak areas (e.g., $A_l(i)$ and $A_r(i)$) are compared to see whether they are within the minimum and the maximum time difference as specified. The minimum and maximum time differences can be adjusted depending on the median flow velocity of the fluid medium. Once a pair of matching integrated peaks from the first and the second detection zones is found, the time difference (i.e., TimeDiff or $\Delta t$) is determined. The time difference is inversely proportional to the analyte flow velocity and is the difference in time when the particle crosses (i.e., detected by) the first and second detection zones. The velocity independent integrated peak area is then calculated by averaging the integrated peak areas of the particle from the first and the second detection zones and dividing the average integrated peak area by time difference. This calculation can be represented by the following formula:

$$A_{vi}=[A_l+A_r/2]\Delta t$$

where $A_{vi}$ is velocity independent area, $A_l$ is integrated peak area from the first detection zone, $A_r$ is integrated peak area from the second detection zone and $A_t$ is time difference. In FIG. 8, the time difference is determined by dividing the difference in point number of $A_l$ and $A_r$ with the sampling rate (i.e., the frequency of switching the laser beam to and from the first and the second detection zones).

Since the velocity independent peak area is determined by averaging the two integrated peak areas from the first and the second detection zones, the apparatuses and methods of the present invention reduces the noise significantly. Moreover, any integrated peak from one detection zone that does not have a corresponding integrated peak on the second detection zone or vice versa is eliminated resulting in further reduction of noise. In conventional single detection method, such peaks are often mistaken as an actual signal, thereby resulting in misinterpretation of the data. By comparing the signals from one detection zone to the other, methods of the present invention further reduces noise or false signals.

It should be appreciated that while the present invention has been described with respect to using a single laser beam with two acousto-optic modulators to guide the laser beam into two scanning detection zones, other arrangements are also possible and are within the scope of the present invention. For example, apparatus of the present invention can be fabricated to utilize two laser beams directed at different detection zone and having a separate acousto-optic modulator for scanning the entire width of the fluid flow channel. In addition, other electromagnetic wave diffracting devices, such as rotating mirrors, gratings and other electromagnetic wave diffracting devices known to one skilled in the art, can be used instead of an acousto-optic modulator. Other variations include using two detectors with either one or two laser beams. If one laser beam is used, it can be split or scanned (i.e., guided) at two different position as described herein, for example, with AO, mirror or other suitable means. If two lasers are used, no scanning is necessary as each laser can be used to illuminate different detecting area. These setup variations offer easier data acquisition and analysis; however, in some cases may result in more complicated alignment of each components.

Moreover, the control over the line scans (i.e., detection zones), which is done by controlling the AOs, is done electronically and can be changed depending on a particular application. For example, the two line scans can be easily rotate by 90 degrees to enable the same measurement in a perpendicular channel. This general measurement method can be used to measure the velocity of particles in a variety of microfluidic devices without the need for any changes in the design of microfluidic devices.

Microfluidic Device

Apparatuses of the present invention also comprise a fluidic device, preferably a microfluidic device, which comprises a fluid flow channel. The fluid flow channel allows flows of the fluid medium from one location to another location within the device. Preferably, the cross-section of the fluid flow channel should be small enough such that only a very small area is scanned by a laser. In general, any microfluidic device made of a material that is transparent to the laser beam is suitable. However, a particularly preferred microfluidic devices are those disclosed by Unger et al. in *Science*, 2000, 288, 113-116, and U.S. patent application Ser. No. 09/605,520, which were incorporated by reference above.

In particular, microfluidic devices which comprise a peristaltic pump is particular useful in the present invention as they allow one to control the median fluid medium flow velocity. However, it should be appreciated that the fluid medium can be made to flow through the fluid channel by any of the conventional means, such as pressure gradient, electroosmotic flow, and the like.

Utility

Apparatuses and methods of the present invention have a wide variety of application such as flow cytometry, oligonucleotide sorting, oligonucleotide analysis, detecting changes in cells, analyzing chromosome distribution in cells (e.g., karyotyping), studying epidemiology, and other diagnostic and assay procedures. Using microfluidic devices in cell and DNA sorting are general described by Fu et al. in "A Microfabricated Fluorescence-activated Cell Sorter," *Nature Biotech.*, 1999, 17, 1109-1111; and Chou et al. in "A Microfabricated Device for Sizing and Sorting DNA Molecules," *Proc. Natl. Acad. Sci. USA*, 1999, 96, 11-13, respectively, which are incorporated herein by reference in their entirety. Methods for cell sorting using microfluidic devices are further detailed in PCT Publication No. WO 99/61888, which is also incorporated herein by reference in its entirety.

In one particular embodiment, methods of the present invention provides determining number of nucleotides that is present in an oligonucleotide. The method generally involves modifying the oligonucleotide by attaching a fluorescent molecule to the oligonucleotide and measuring a velocity independent integrated fluorescent peak area. This velocity independent integrated fluorescent peak area is then compared with a velocity independent integrated fluorescent peak area of a standard oligonucleotide having a known number of nucleotides. Preferably, velocity independent integrated fluorescent peak areas are determined for a number of standard oligonucleotides having a different number of nucleotides. In this manner, a calibration table can be produced and used to determine the number of nucleotides present in an oligonucleotide.

The modified oligonucleotide and the standard oligonucleotides are attached with a known amount of fluorescent molecules per given number of nucleotides. In this manner, a given velocity independent integrated fluorescent peak area can be calibrated to represent a certain number of nucleotides that is present in the oligonucleotide.

Additional objects, advantages, and novel features of this invention will become apparent to those skilled in the art upon examination of the following examples thereof, which are not intended to be limiting.

Experimental

Apparatus

The fluorescence excitation was performed with a 5 mW, 488 nm laser beam from an air cooled argon ion laser (Uniphase, San Jose, Calif.). The laser beam was transmitted through two mutually orthogonal acousto-optic (AO) modulators to produce two line scans (see FIG. 2A). Each AO was driven by voltage controlled oscillator (VCO) connected to a function generator. The first AO was oriented so as to move the beam in the x direction, parallel to the direction of the flow. Its VCO was driven with a square wave (5 KHz, 7 $V_{p-p}$) causing the beam to move between two points along the channel. The second AO was oriented to enable moving of the beam in the Y direction, thus allowing the beam to cross the channel. The signal that was used to control this AO was a sinusoidal wave (120 KHz, 9 $V_{p-p}$) at a frequency higher than the chopping signal to ensure several crossing of the channel for each position on the x direction. At the exit of the second AO the original laser beam was divided into a grid of beams (see FIG. 2C). Most of these beams were blocked leaving out only the beam that was the combination of the first orders of both AOs. This beam was thus scanned along two parallel lines (left and right line scans) in different positions along the flow. The laser beam was focused through a 100×1.3NA oil immersion objective (Olympus, New Hyde Park, N.J.) which also was used to collect the emitted fluorescence. The full width half maximum of the beam at the channel was about 1 µm. Auxiliary lenses were used to adjust the distance between the two scan lines as well as their length to be in the order of 10 µm. The uniformity of the excitation across the channel was not dependent on the beam size but rather on the uniformity of the illumination while the beam was scanned. This was evaluated by imaging a thin layer of fluorescein in solution illuminated by the scanning beam with a CCD camera (see FIG. 2B, left portion). The image was then digitized and evaluated for uniformity. A dichroic filter was used to introduce the laser light into the optical train (Chroma 500 DCLP, Chroma Technology, Brattleboro, Vt.). Dielectric filter was used to reduce background and scattered light from the emitted fluorescence (Chroma D535/50M). The fluorescence was imaged onto a channel photomultiplier detector (EG&G, Gaithersburg, Md.). The detector output as well as the chopping square wave were digitized at a rate of 40 KHz by a National Instrument (Austin, Tex.) Lab PC1200 board on a personal computer running LABVIEW.

Microfluidic Device

A 3.9 µm high, 5 µm wide rectangular fluid flow channel was fabricated from a silicon elastomer (General Electric RTV 615) by using a replica technique generally disclosed by Chou et al., in *Proc. Nat. Acad. Sci. USA*, 1999, 96, 11-13 and U.S. patent application Ser. No. 09/605,520, filed Jun. 27, 2000, which were previously incorporated by reference in their entirety. Master molds were made from silicon wafers by using standard micromachining techniques.

Data Analysis

Both line scans were well inside the detecting area, thus the fluorescence signals from both line scans were recorded as one signal. However, since the excitation beam was scanning, the obtained fluorescence light originated from only one line scan. Thus, by simultaneously recording the data signal and the chopping square signal, it was possible to separate the data signal to two separate subsignals, one from each line scan (see flow chart in FIG. 7). Each of these signals (5 KHz) was individually analyzed off line with a computer program to obtain the position in time and area of each peak in the signals.

As shown in the flow chart in FIG. 8, the positions of the peaks from both subsignals were used to match pair of peaks, one from each line scan, that were assumed to arise from the same fluorescent molecule. Then for each pair the time difference between the positions of its two peaks were calculated. The time difference is inversely proportional to the velocity of the molecule. The average area of each pair of peaks was normalized by dividing it by the corresponding time difference. Thus, for each pair of peak, which arises from one particle, the normalized total fluorescence and the velocity were obtained.

EXAMPLE 1

This example illustrates the method of measuring flow velocity of particles.

Figure 5:
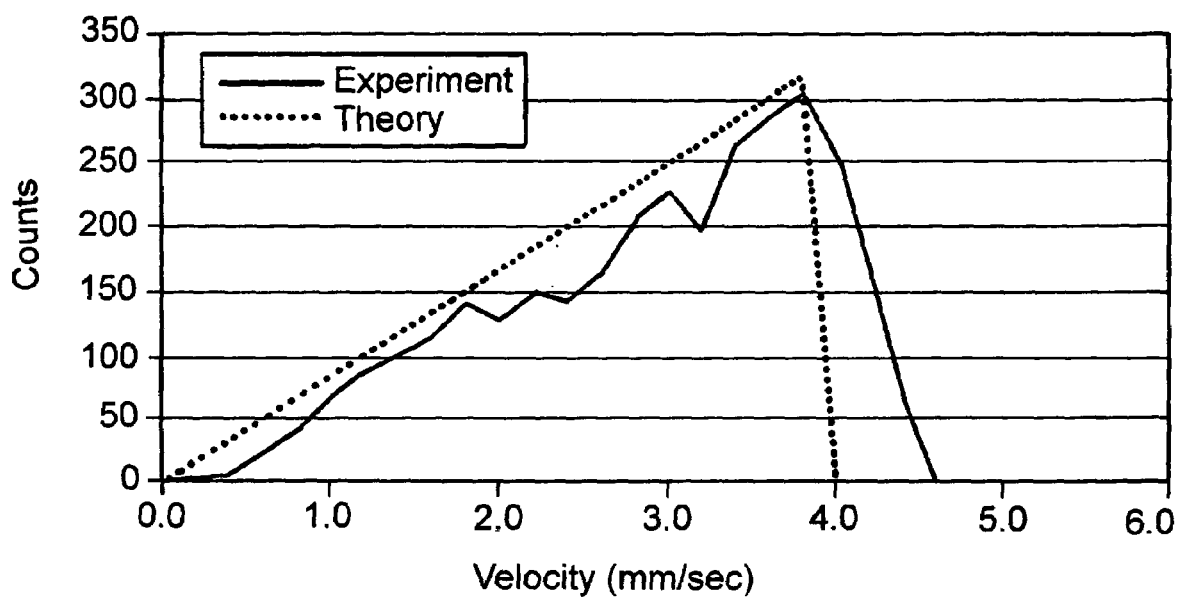
FIG. 5 shows histogram of the velocities of 0.2 µm fluorescent beads that were in the system (solid line) and the corresponding theoretical one (dash line).

A solution of fluorescent beads (FluoSpheres Biotin Labeled microspheres 0.2 µm, yellow green fluorescent, Molecular Probes) were introduce into the microfluidic device and their velocity were measured. The flow of fluorescent beads was achieved by capillary flow in the microfabricated channels sealed by coverslips. A histogram of the bead flow velocities is seen in FIG. 5 for a later time in the experiment in which the transient stage is over and the velocity distribution become roughly constant. Assuming uniform distribution of beads in the channel, the theoretical probability, $P_{pr}$, of a particle with velocity $v_0$ to pass through the cross section in a given time is given by the equation:

$$P_{pr}(v = v_0) = \frac{v_0 P_v(v = v_0)}{\int v P_v dv}$$

where $P_v$ is the probability to have a velocity v in the cross section of the channel. In circular tubes $P_v$ is constant for $v < v_{max}$ for Poiseuille flow. The rectangular cross section of the fluid flow channels of the microfluidic device had an aspect (i.e., width to length) ratio of 1.3; therefore, only minor changes to $P_v$ is introduced compare to a circular cross section fluid flow channel. Therefore, as a first order approximation the theoretical $P_{pr}$ is proportional to v for $v < v_{max}$. This theoretical result is substantially in agreement with the experimental results. See FIG. 5. The high correlation between the two graphs shows that velocity can be accurately determined using an apparatus and a method of the present invention.

EXAMPLE 2

In the next experimental stage a solution of a mix of two kinds of beads (Component A and B, LinearFlow green flow cytometry intensity calibration kit, 2.5 µm, Molecular Probes) which were similar in every other aspect besides their fluorescent intensity was introduce to the system. The fluorescent intensity of the beads was collected by the channel photomultiplier for a period of 400 sec. For each passing particle, the normalized area and velocity were calculated.

Figure 4:
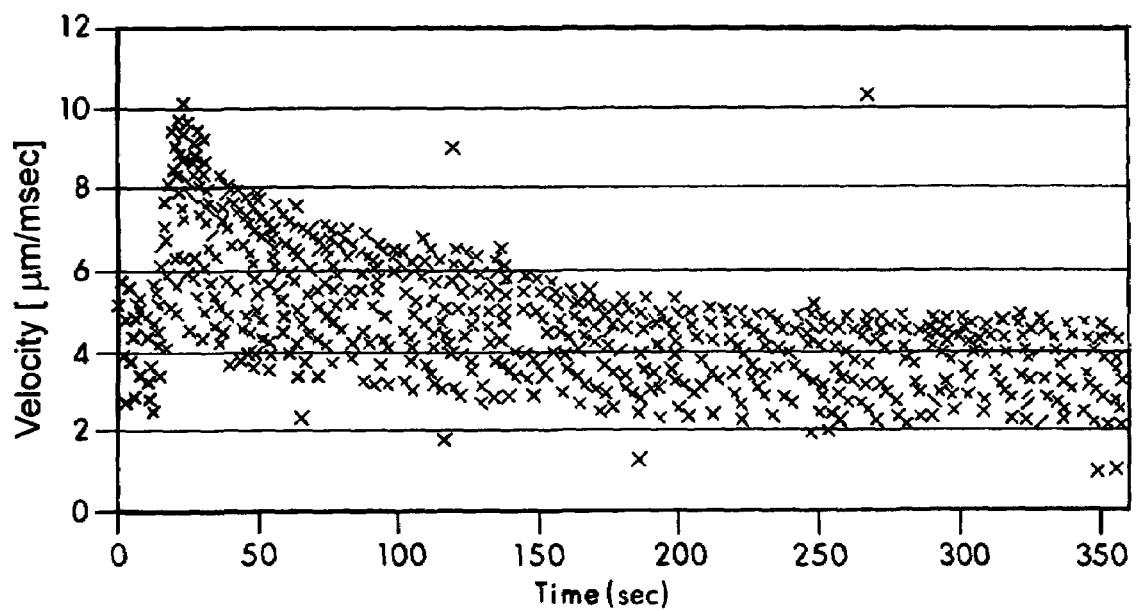
FIG. 4 shows the velocity as a function of time of an experiment with the same two kinds of fluorescent beads as in FIG. 3.

The velocity as a function of time was plotted. See FIG. 4. The flow in the system is capillary flow and is driven by the pressure difference between the ends of the channel. During the time of the experiment, the pressure at the beginning of the channel, originating from the fluid at the starting basin, decreases while the pressure at the output increases. This pressure change results in a decay in the velocity over time, as shown in FIG. 4 (t>20 sec). The abrupt change in the velocity, which occurs at about 20 sec, corresponds to the arrival of the fluid front to the output end of the fluid flow channel.

A histogram of the peak areas and the normalized peak areas was plotted. As shown in FIG. 3, without normalization it is difficult to distinguish between the two kinds of beads. The coefficient of variance (CV) of the peaks were improved by the normalization from about 24% and 18% to 9.75% and 5.18% for the two kinds of beads, respectively.

An extra peak in the histogram is seen only in the graphs from the single line scan at the lower area region, which is believed to be associated with noise. Many of the noise peaks that were found in each line scans signal can not be paired with correlating peaks from the other channel. Thus, the additional low peak in the histogram is missing for the normalized areas one, which shows that the normalization method reduces noise significantly.

EXAMPLE 3

Lambda phage DNA (GIBCO) was diluted in buffer (Tris EDTA, pH 6.8 with 5 mM NaCl) and stained with the intercalating dye $C_{49}H_{58}I_4N_6O_2$, marketed as YOYO®-1 (Molecular Probes) at a stochiometry of one dye molecule per 4 bp.

Figure 6:
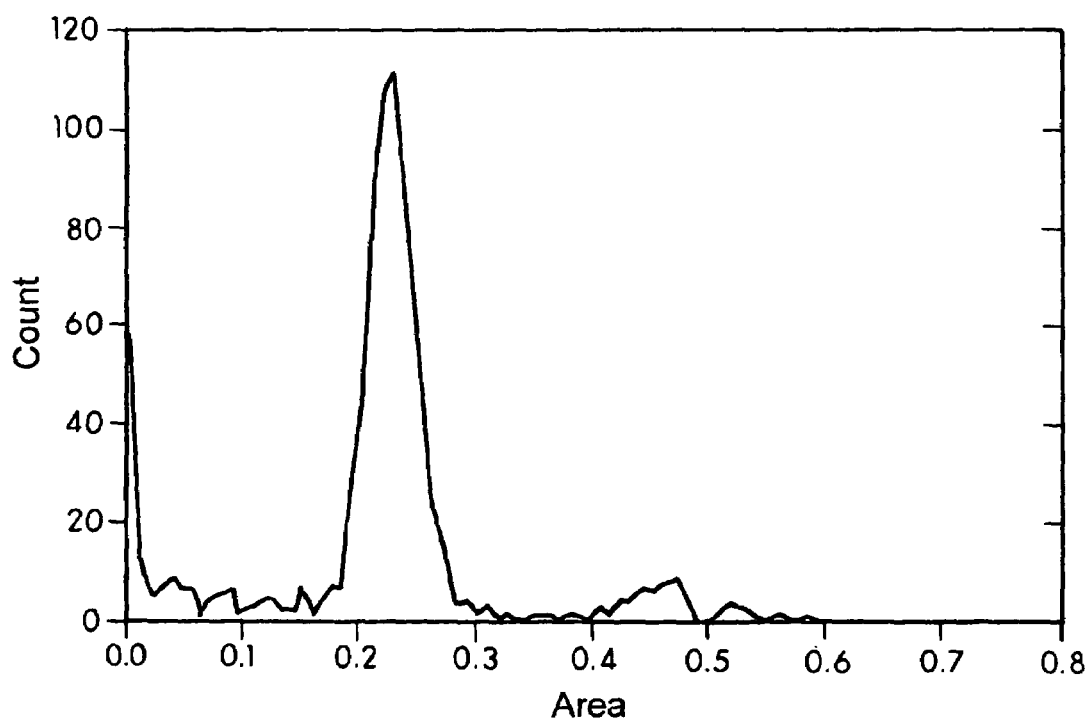
FIG. 6 shows histogram of λ DNA, where the center peak represents λ DNA (48 kbp) and the small peak on the right represents pairs of hybridized λ (96 kbp).

Then a solution of stained $\lambda$ DNA was introduced to the microfluidic device for a period of 5 minutes. A histogram of the normalized areas of the molecules is plotted and is shown in FIG. 6. The center peak in the histogram corresponds with the $\lambda$ DNA (48 kbp) and the small peak in the right corresponds with hybridized pairs of $\lambda$ DNA (96 kbp), i.e., $\lambda^2$. The CV for the $\lambda$ and $\lambda^2$ peaks were 8.34% and 7.61%, respectively, and the ratio between the centers of the two peaks was 2.06.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for determining a characteristic parameter of an analyte, wherein the characteristic parameter of the analyte is independent of a flow velocity of the analyte, but a measurement of the characteristic parameter of the analyte is capable of being influenced by or dependent on the velocity of the analyte, said method comprising:
   (a) transporting a fluid medium comprising the analyte from a first position to a second position of a fluid flow channel of a fluidic device;
   (b) measuring the characteristic parameter of the analyte within the fluid flow channel at a plurality of different detection zones separated along a flow path of the analyte in between the first and the second positions;
   (c) determining a velocity dependence of the measurement of the characteristic parameter; and
   (d) determining the characteristic parameter of the analyte independent of the flow velocity of the analyte by using the measurements of the characteristic parameter of step (b) and normalizing the measurements of the characteristic parameter by substantially eliminating the velocity dependence of the measurements of the characteristic parameter.

2. The method of claim 1, wherein said fluidic device is a microfluidic device.

3. The method of claim 2, wherein transporting the fluid medium comprises transporting the fluid medium with a peristaltic pump or by electroosmosis.

4. The method of claim 1, wherein the characteristic parameter of the analyte is measured in step (b) with a laser beam guiding device that comprises an acousto-optic modulator.

5. The method of claim 1, wherein the analyte is a cell, an oligonucleotide or an organic compound.

6. The method of claim 5, wherein the analyte is a cell and said method is used for cell sorting.

7. The method of claim 5, wherein the analyte is an oligonucleotide and said method comprises determining the number of nucleotides in the oligonucleotide.

8. The method of claim 7, wherein said step of determining the number of nucleotides in the oligonucleotide comprises:
   (A) attaching a fluorescent molecule to the oligonucleotide to produce a modified oligonucleotide prior to measuring velocity independent characteristic parameter of the modified oligonucleotide, wherein said characteristic parameter is an integrated fluorescent peak area of said modified oligonucleotide; and
   (B) determining the number of nucleotides in the oligonucleotide by comparing the velocity independent integrated fluorescence peak area of the modified oligonucleotide with a velocity independent fluorescence peak area of a standard oligonucleotide, wherein the velocity independent fluorescence peak area of the standard oligonucleotide has been calibrated to the number of nucleotides present the standard oligonucleotide.

* * * * *